(12) United States Patent
Mott et al.

(10) Patent No.: US 9,189,739 B2
(45) Date of Patent: Nov. 17, 2015

(54) METHODS AND SYSTEMS FOR CIRCADIAN PHYSIOLOGY PREDICTIONS

(71) Applicants: Christopher Grey Mott, Seattle, WA (US); Guy DuMont, Vancouver (CA); Diane Boivin, Montreal (CA); Daniel Joseph Mollicone, Seattle, WA (US)

(72) Inventors: Christopher Grey Mott, Seattle, WA (US); Guy DuMont, Vancouver (CA); Diane Boivin, Montreal (CA); Daniel Joseph Mollicone, Seattle, WA (US)

(73) Assignee: Pulsar Informatics, Inc., Philadelphia, PA (US)

( * ) Notice: Subject to any disclaimer, the term of this patent is extended or adjusted under 35 U.S.C. 154(b) by 0 days.

(21) Appl. No.: 13/919,703

(22) Filed: Jun. 17, 2013

(65) Prior Publication Data
US 2013/0282646 A1 Oct. 24, 2013

Related U.S. Application Data

(63) Continuation of application No. 12/626,846, filed on Nov. 27, 2009, now Pat. No. 8,484,153.

(51) Int. Cl.
*G06N 7/00* (2006.01)
*G06N 5/02* (2006.01)
*A61B 5/00* (2006.01)
*G06F 19/00* (2011.01)

(52) U.S. Cl.
CPC ............. *G06N 5/02* (2013.01); *A61B 5/4857* (2013.01); *A61B 5/7264* (2013.01); *G06F 19/3437* (2013.01); *G06N 7/005* (2013.01)

(58) Field of Classification Search
CPC ......................................... G06N 7/005
USPC .......................................... 706/52
See application file for complete search history.

(56) References Cited

PUBLICATIONS

Brown et al ("A mathematical model of diurnal variations in human plasma melatonin levels" 1997).*
Zeitzer et al ("Sensitivity of the human circadian pacemaker to nocturnal light: melatonin phase resetting and suppression" Journal of Physiology 2000).*

* cited by examiner

*Primary Examiner* — Lut Wong
(74) *Attorney, Agent, or Firm* — Damian M. Biondo, Esq.

(57) ABSTRACT

Systems and methods are provided for predicting a circadian state of an individual. The methods comprise: providing a model representative of the response of the circadian state to light stimulus, the model comprising at least one model variable representative of a probability distribution function (PDF) of a phase offset of the circadian state of the individual; and using the model to estimate an updated PDF of the phase offset, wherein using the model to estimate the updated PDF of the phase offset comprises performing a Bayesian estimation process commencing with an initial PDF of the phase offset and iterating toward the updated PDF of the phase offset.

22 Claims, 19 Drawing Sheets

PREDICTION UPDATE PROCEDURE (BLOCK 204)

Algorithm 2 Prediction Update

1: procedure $[x_k^i]$ = INCREMENT$(x_{k-1}^i, u_{k-1}, z_k, Q_k, R_k)$
2:     $H = \nabla h(x_{k_1})$
3:     $S = HQ_kH' + R_k$
4:     $\Sigma = Q_k - Q_kH'S^{-1}HQ_k$
5:     for $i = 1 : N$ do
6:         $\tilde{x}_k^i = f(x_{k-1}^i, u_{k-1})$     ▷ prediction update
7:         $\tilde{z}_{k-1}^i = h(\tilde{x}_k^i, u_{k-1})$
8:         $\hat{x}_k^i = \tilde{x}_k^i + \Sigma H'R_k^{-1}\text{MODMINUS}(z_k, \tilde{z}_{k-1}^i, 24)$     ▷ measurement update
9:         Draw $x_k^i \sim \mathcal{U}(\hat{x}_k^i, \text{diag}\Sigma)$     ▷ draw $x_k^i$ from $p(x_k|x_{k-1}^i, z_k)$
10:    $x_k^i(2) = \text{mod}(x_k^i(2), 24)$     ▷ keep phase within $[0, 24)$
11:    end for
12: end procedure

FIGURE 12A

IMPORTANCE WEIGHT PROCEDURE (BLOCK 222)

Algorithm 3 Measurement Update

1: procedure $[w_k^i]$ = IMPORTANCEWEIGHT$(x_k^i, z_k, Q_k, R_k)$
2:     $S = HQ_kH' + R_k$
3:     for $i = 1 : N$ do
4:         $\hat{z}_k^i = h(x_k^i, u_k)$
5:         $d_\varphi = \text{MODMINUS}(z_k, \hat{z}_k^i, 24)$     ▷ phase difference using modulo
6:         $w_k^i = \mathcal{N}(d_\varphi; 0, S(2,2))$     ▷ set particle weight to $p(z_k|x_k^i)$
7:     end for
8:     for $i = 1 : N$ do
9:         $w_k^i = w_k^i / \Sigma_{i=1}^N w_k^i$     ▷ normalize the weights
10:    end for
11: end procedure

FIGURE 12B

RESAMPLE PROCEDURE (BLOCK 224)

Algorithm 4 Systematic Resampling

```
 1: procedure [x_k^i, w_k^i] = RESAMPLE(x_k^i, w_k^i)
 2:     j = 1
 3:     C = N^{-1}
 4:     CSW = 0
 5:     while C < 1 do
 6:         if CSW > C then
 7:             C = C + N^{-1}
 8:         else
 9:             select i randomly from [j, N]
10:             CSW = CSW + w_k^i              ▷ increment cumulative sum of weights
11:             x_k^i = x_k^j                   ▷ swap new particle
12:             j = j + 1
13:         end if
14:     end while
15:     for i = 1 : N do
16:         w_k^i = N^{-1}                      ▷ set weights to uniform values
17:     end for
18: end procedure
```

FIGURE 12C

MARKOV CHAIN MONTE CARLO MOVE (BLOCK 226)

Algorithm 5 Markov chain Monte Carlo Move

```
 1: procedure [x_k^i] = MCMC-MOVE(x_k^i, u_k, Q_k, R_k)
 2:     S = HQ_k H' + R_k
 3:     for i = 1 : N do
 4:         ẑ = h(x_k^i, u_k)
 5:         d_φ = MODMINUS(z_k, ẑ_k^i, 24)
 6:         L^i = N(d_φ; 0, S)                  ▷ likelihood of current particle p(z_k|x_k^i)

7:         draw x̃_k^i ~ U(f(x_{k-1}^i, u_k), Q_k)   ▷ generate a new random proposal
 8:         z̃ = h(x̃_k^i, u_k)
 9:         d_φ = MODMINUS(z_k, ẑ_k^i, 24)
10:         L̃^i = N(d_φ; 0, S)                 ▷ likelihood of proposed particle p(z_k|x̃_k^i)

11:         P_a = min(1, L^i/L̃^i)              ▷ probability of acceptance of new particle
12:         draw r ~ [0, 1]                     ▷ random number from 0 to 1
13:         if P_a ≥ r then
14:             x_k^i = x̃_k^i                  ▷ replace x with new proposal
15:         end if 16:     end for
17: end procedure
```

FIGURE 12D

NO SLEEP HISTORY INFO

METHODS AND SYSTEMS FOR CIRCADIAN PHYSIOLOGY PREDICTIONS

RELATED APPLICATIONS

This application is a continuation of U.S. application Ser. No. 12/626,846 with a filing date of Nov. 27, 2009 issued as U.S. Pat. No. 8,484,153 on 9 Jul. 2013, which in turn is a continuation-in-part of PCT application No. PCT/CA2008/001007, with an international filing date of 29 May 2008, which in turn claims priority from U.S. application No. 60/932,102 filed 29 May 2007. All documents cited within this paragraph are hereby incorporated herein by reference.

TECHNICAL FIELD

The invention relates to systems and methods for tracking the state of a subject's circadian physiology. Particular embodiments provide state estimation systems and methods which combine mathematical models of circadian physiology, measurements of incident light, and measurements of physiological parameters to generate statistical estimates of circadian states.

BACKGROUND

The word "circadian" is derived from the Latin words circa, meaning about, and dies, or day and refers to processes with 24 hour rhythms. Circadian physiological rhythms are present in organisms across the animal and plant kingdoms. Circadian rhythms are thought to be driven by an internal pacemaker that maintains a self-regulating oscillation with a 24 hour period. Recent research has revealed the molecular structures which form the core of the human circadian pacemaker. The pacemaker serves as a central timing mechanism which synchronizes the rhythms of a wide array of physiological systems.

Circadian Pacemaker Mechanism

Daily fluctuations in human physiology, such as sleeping and body temperature changes, have long been observed; however, it was not until the 1970s that strong experimental evidence of the existence in humans of an endogenous circadian pacemaker emerged. Subsequently, in the 1990s the molecular basis of a central human circadian pacemaker was identified. More specifically, research indicates that a molecular clock located in the suprachiasmatic nucleus (SCN) in the hypothalamus region of the brain maintains an approximate 24 hour rhythm. While evidence of additional peripheral oscillators exists, such as in the liver, the SCN pacemaker is believed to play the central role in regulating circadian timing signals for other physiological systems.

Although the circadian pacemaker has an intrinsic period close to 24 hours, precise synchronization to the external environment is maintained by external stimuli referred to as "zeitgebers" (from German zeit (time) and geber (giver)). For most organisms, including humans, the strongest known zeitgeber is light. The daily transitions between light and dark caused by the earth's rotation relative to the sun create a strong environmental stimulus to which organisms naturally synchronize.

Synchronization of the circadian pacemaker to light occurs through photoreceptors in the retina which have a neural pathway to the SCN that is distinct from the neural pathway of the visual system. Signals arriving to the SCN modify both the phase and amplitude of the pacemaker's oscillations. The duration, intensity, timing of light exposure relative to circadian phase and the pattern of light exposure are all factors which have been observed to influence an organism's circadian pacemaker.

Studying the effects of circadian rhythms is generally not as straight forward as considering 24 hour physiological oscillations. Daily patterns of physical activity and sleep-wake also generally occur on a 24 hour schedule, so it is desirable to distinguish between behavior-induced rhythms (e.g. body temperature rising during the day because of walking) and endogenously driven rhythms (e.g. body temperature rising based on internal circadian thermoregulatory signals).

Two predominant experimental techniques for isolating circadian effects are referred to as the "forced desynchrony" and "constant routine" protocols. Both occur in time isolation laboratories. The forced desynchrony technique forces an individual's sleep and wake schedules to desynchronize from their internal circadian pacemaker. The constant routine technique eliminates sleep/wake effects by keeping individuals awake in a constant environment for more than 24 hours. Based on studies conducted with these protocols, a number of relationships between the circadian pacemaker and various physiological systems has been identified. Non-limiting examples of physiological systems that are, or may be, effected by, or otherwise related to, the circadian pacemaker include: core body temperature (CBT), hormonal melatonin concentration, hormonal cortisol concentration, rate of cell proliferation, the cardiac regulatory system, chemoreceptive respiratory feedback system and cognitive performance (alertness).

Indirect Measurement of Circadian State

Since the human central circadian pacemaker mechanism is inaccessibly located in the brain, its state cannot be measured directly. Some researchers have attempted to indirectly measure a subject's circadian state by inferring the subject's circadian state from measurements of downstream physiological systems. A complication arising out of such indirect inference is that systems with an observable circadian modulation, such as CBT and melatonin secretion for example, are also responsive to other physiological systems and/or environmental stimulus. From the perspective of attempting to infer a subject's circadian state, such physiological systems and/or environmental stimulus are considered to mask the circadian contribution to the observed physiological system. Accordingly, most indirect measurements of a subject's circadian state require methods to "demask" the circadian signal components of an observable system from the other, non-circadian components. Two demasking approaches which have been used in the past involve: physical elimination of time-varying exogenous stimulus; and extraction of exogenous factors using signal processing techniques. Laboratory protocols associated with holding all exogenous stimuli constant may be referred to as "constant routine" techniques. Signal processing methods for extracting exogenous factors may be referred to as "purification" techniques.

The Constant Routine Technique

CBT and hormonal melatonin levels are two physiological systems that tend to exhibit consistent and observable circadian rhythms. However, CBT also responds to physical activity, posture, ambient temperature, and sleep and melatonin secretion is also responsive to ambient light exposure. A constant routine demasking procedure developed by Czeisler (Czeisler, C., J. Allan, S. Strogatz, E. Ronda, R. Sanchez, C. Rios, G. Freitag, G. Richardson, and R. Kronauer, Bright light resets the human circadian pacemaker independent of the timing of the sleep-wake cycle. Science 233:4764, 667-671; 1986 (Czeisler 1986)) attempts to minimize such confounding effects on CBT and melatonin levels, by placing subjects in a strictly controlled laboratory environment. To reduce the effects of sleep-wake transitions and posture changes, the Czeisler technique typically involves: keeping subjects awake for long periods of time (e.g. up to 40 hours) in a semi-recumbent position; setting light exposure to a low level (e.g. to 10 lux); introducing meals at regular intervals (e.g. one hour intervals); and limiting physical activity.

During the constant routine technique, CBT may be measured continuously and the circadian contribution to the CBT (a roughly sinusoidal oscillation with an amplitude of approximately 2° C.) may be monitored. The timing of the minimum of this approximately sinusoidal CBT oscillation typically occurs between 4:00 AM and 5:00 AM and is may be used as an indicator of the circadian state of a subject. The natural circadian melatonin cycle includes an onset in secretion approximately at one's typical sleep time. The timing of this onset is driven by the circadian pacemaker; however, melatonin secretion is also affected by exposure to ambient light. The dim light conditions of the constant routine technique facilitate measurement of the Dim Light Melatonin Onset (DLMO) time.

The constant routine technique is currently accepted as a state of the art method for experimentally assessing the circadian state of a subject and is the primary method by which data have been collected about the circadian-phase-shifting effects of light. Despite the success of the constant routine technique, its application is limited to laboratory environments and often involves subject discomfort (e.g. having to be awake for 40 hours).

The Purification Technique

The "purification" demasking approach is another method of circadian state estimation which attempts to use signal analysis techniques to remove masking contributions from observed physiological phenomena (i.e. to extract the circadian contribution from the observed physiological phenomena). Typically, purification techniques attempt to avoid the restrictive physical constraints of the constant routine technique. Physical activity and sleep represent two well-known masking factors associated with the observable phenomena of CBT. Consequently, prior art purification methods have focused on the separation of the effects physical activity and sleep contributions to CBT from the circadian component contribution to CBT. In contrast to the constant routine technique, participants in purification studies have been allowed to follow regular sleep/wake schedules with free ambulatory movement during waking periods.

Waterhouse has developed statistical methods of purification utilizing data from activity sensors. One method involves categorizing activity during waking and sleep periods and then calculating an associated temperature effect from each activity category (Waterhouse, J., D. Weinert, D. Minors, S. Folkard, D. Owens, G. Atkinson, D. Macdonald, N. Sytnik, P. Tucker, and T. Reilly, A comparison of some different methods for purifying core temperature data from humans. Chronobiology International 17:4, 539-566; 2000 (Waterhouse 2000A)). A second method uses a linear regression based on direct mean scores from activity sensors (Waterhouse 2000a). Recent developments in purification-based methods have introduced some basic thermoregulatory models (Weinert, D., A. Nevill, R. Weinandy, and J. Waterhouse, The development of new purification methods to assess the circadian rhythm of body temperature in mongolian gerbils. Chronobiology International 20:2, 249-270; 2003).

While results using purification techniques have been shown to be comparable to constant routine techniques in some cases (Waterhouse, J., S. Kao, D. Weinert, B. Edwards, G. Atkinson, and T. Reilly, Measuring phase shifts in humans following a simulated time-zone transition: Agreement between constant routine and purification methods. Chronobiology International 22(5), 829-858; 2005), there remains contention among experts about the accuracy of purification approaches relative to constant routine techniques. A significant limitation of the statistical purification approach is that during periods of significant desynchrony between sleep-wake times and circadian phase, linear methods to separate the two effects from CBT data are inherently unreliable.

Actigraphy

Another approach to indirectly measuring the circadian state of an individual is referred to as actigraphy and is based on the assumption that there is a direct correlation between an individual's rest-activity rhythm and their sleep-wake rhythm and thus their circadian state. Actigraphy involves recording of rest-activity patterns using sensors which record gross physical movement. Typically, actigraphs are implemented using wrist-worn accelerometers.

Actigraphy has been used to indirectly measure the circadian state of cancer patients for timing the delivery of chronomodulated chemotherapy drugs. The type of circadian variation present in actigraph measurements has also been shown to provide an indicator of 'health status' of cancer patients. Actigraphy appears attractive for use in field applications, since it is portable and generally non-invasive. However, studies to date have yet to produce strong evidence demonstrating the link between actigraphy and more direct physiological systems known to be correlated to circadian state (e.g. CBT or melatonin). Actigraphy-based techniques have been applied only to individual's following a regular diurnal schedule. As such, confounding factors such as inter-individual variations in circadian phase, differences in behavioral patterns, and irregular schedules, such as arise with shift-work or the like, limit the accuracy and precision of actigraphy-based techniques.

Modeling and Predicting Circadian Dynamics

An alternative to measurement of observable physiological phenomena and using such physiological measurements to estimate an individual's circadian state involve the use of predictive models of circadian pacemaker physiology. Mathematical models describing the dynamic response of the circadian pacemaker have been used to predict the behavior of the circadian pacemaker under specific light exposure scenarios.

Mathematical Models of Circadian State

The most widely accepted model of the circadian pacemaker was developed by Kronauer et al in 1987 based on observations of dose-response relationships between light exposure and circadian phase shifts. Kronauer inferred from experimental data that the model should have both a self-regulating oscillator component representing the internal circadian pacemaker, and a light input response component representing the pathway from light in the eye to a synchronizing input on the oscillator. Subsequent discovery of the molecular functionality of the circadian pacemaker has supported the general physiological basis of the Kronauer model. A refined version of the Kronauer model (the Kronauer-Jewett model) was published in 1999 (Jewett, M., D. Forger, and R. Kronauer, Revised limit cycle oscillator model of human circadian pacemaker. Journal of Biological Rhythms 14:6, 493-499; 1999 (Jewett 1999b)).

FIG. 1 represents a schematic, block-diagram depiction of the Kronauer-Jewett model 10, which comprises a dynamic model including a circadian pacemaker component 12 and a physiological marker component 14 for comparison to a measurable physiological parameter. In the prior art Kronauer-Jewett model 10 of FIG. 1, the measurable physiological parameter is the subject's CBT. Circadian pacemaker component 12 of the Kronauer-Jewett model 10 receives a light input I together with a set of initial conditions $x_{init}$, $x_{c\ init}$ and $n_{init}$ corresponding to its model variables x, $x_c$ and n and uses this information together with its model equations to generate output model variables x, $x_c$. Typical profiles of output model variables x, $x_c$ are shown in FIG. 2. It may be observed that output model variables x, $x_c$ are approximately sinusoidal in shape with a period of approximately 24 hours and that output model variables x, $x_c$ are approximately 90° out of phase with one another.

Physiological marker component 14 of the Kronauer-Jewett model 10 incorporates a minimizer component 16. Minimizer component 16 receives the output model variable x and returns a time at which output model variable x is a minimum $x_{min}$. As shown in FIG. 2, the minimum $x_{min}$ (also referred to as a nadir of the model variable x) occurs once every period of output model variable x or approximately once every 24 hours. The time at which output model variable x is a minimum $x_{min}$ is referred to FIGS. 1 and 2 as $\phi_{min}\{x\}$.

The Kronauer-Jewett model 10 also incorporates the experimentally determined observation that the time $\phi_{min}\{x\}$ that the model variable x is a minimum $x_{min}$ is correlated to the time of the CBT minimum $CBT_{min}$. The time that physiological marker component 14 predicts to be the time of $CBT_{min}$ is referred to in FIG. 1 as $\phi_{min}\{CBT\}$. As can be seen by observation of summing junction 18, the Kronauer-Jewett model 10 incorporates the experimentally determined relationship that the time $\phi_{min}\{CBT\}$ typically occurs 0.8 hours after the time $\phi_{min}\{x\}$. Physiological marker component 14 of the Kronauer-Jewett model 10 outputs the time $\phi_{min}\{CBT\}$ of the CBT minimum $CBT_{min}$ which in turn permits comparison of the Kronauer-Jewett model 10 to measured CBT values. Since the time $\phi_{min}\{x\}$ that the model variable x is a minimum $x_{min}$ is only output once every approximately 24 hours, it follows that physiological marker component 14 only outputs the time $\phi_{min}\{CBT\}$ of the CBT minimum $CBT_{min}$ once every approximately 24 hours.

The Kronauer-Jewett circadian pacemaker model 10 has been used with differential-equation-solving algorithms to generate simulations predicting the phase shift of the circadian pacemaker, starting from known initial conditions ($x_{init}$, $x_{c\ init}$, $n_{init}$), in response to a given light exposure pattern (I). This predictive capability has been successfully used to design of experimental protocols and confirm experimental observations of circadian phase shifts in a laboratory context. Despite the apparent usefulness of the Kronauer-Jewett model 10, it has not actually been widely applied in broader contexts—e.g. outside of an experimental laboratory environment.

A number of drawbacks have tended to limit widespread adoption of the prior art Kronauer-Jewett model 10 as a general modeling framework. By way of non-limiting example, such limitations include: (i) the circadian phase of the subject is not presented as a continuous variable which can be monitored (e.g. as an output of model 10) or updated (e.g. as an initial condition of model 10); (ii) the correlation between the circadian phase and physiological marker 14 is not defined in a statistical manner (i.e. Kronauer-Jewett model 10 does not incorporate statistical uncertainties); and (iii) the Kronauer-Jewett model 10 only specifies a correlation to CBT and not to other physiologically observable phenomena.

Alertness Models

One use of circadian physiology models is in the field of human alertness modeling and prediction. Human alertness may also be referred to as human performance. Current models of human alertness incorporate both a sleep-related component and a circadian component; however, most of the widely used human-alertness models assume a fixed circadian phase—e.g. a series of sinusoidal harmonics with a predetermined and constant phase. With such constant phase assumption, scenarios in which the actual circadian phase of a subject may be non-stationary, e.g. shift work or transmeridian travel, cannot be accurately modeled. Some human-alertness models incorporate the potential for changing circadian phase. One such human-alertness model uses a version of the Kronauer model for accommodating variations in the circadian phase (Jewett, M. and R. Kronauer (1999). Interactive mathematical models of subjective alertness and cognitive throughput in humans. Journal of Biological Rhythms 14:6, 588-597; 1999 (Jewett 1999a)). Another such human-alertness model uses a "rule of thumb" for shifting the circadian phase in response to time-zone changes—e.g. a constant rate of change of the circadian phase until the subject is entrained to the new time zone (Akerstedt, T., S. Folkard, and C. Portin, Predictions from the three process model of alertness. AVIATION SPACE AND ENVIRONMENTAL MEDICINE March 75:3, Suppl., A75-A83; 2004). The lack of dynamic circadian modeling has been identified as a general need in the context of human alertness prediction.

One of the challenges in applying a human-alertness model incorporating a detailed dynamic circadian pacemaker model to real world scenarios is that current simulation methods require precise specification of initial conditions and complete knowledge of light levels during the course of the simulation. In uncontrolled environments, such as in an actual workplace or in almost any scenario outside of a laboratory, it is difficult to assess both the circadian phase and ambient light levels for a specific individual. It may be this reason that the Kronauer-Jewett model 10 has found application in simulating laboratory environment scenarios, where circadian phase and light levels can be controlled, but has not been widely used in operational scenarios. This inability to apply circadian predictions to real world environments may be partially responsible for the fact that despite a well-established model of the circadian pacemaker, it remains difficult for scientists to provide definitive advice concerning specific circadian adjustment countermeasures.

There is a general desire for systems and methods for predicting a belief in or probability of the circadian state of a subject which may overcome or ameliorate some of the aforementioned issues with the prior art.

BRIEF DESCRIPTION OF THE DRAWINGS

In drawings which depict non-limiting embodiments of the invention:

FIGS. 12A, 12B, 12C and 12D respectively represent pseudocode procedures for implementing the prediction update, IMPORTANCE WEIGHT, RESAMPLE and MOVE blocks of the FIG. 11 particle filtering method;

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Systems and methods are provided for predicting a circadian state of an individual. The systems and methods may be implemented, at least in part, using a computer or other suitably configured processor. The methods comprise: providing a state-space model representative of the response of the circadian state to light stimulus, the model comprising at least one state variable representative of a probability distribution function (PDF) of a phase offset of the circadian state of the individual; and using the model to estimate an updated PDF of the phase offset, wherein using the model to estimate the updated PDF of the phase offset comprises performing a Bayesian estimation process commencing with an initial PDF of the phase offset and iterating toward the updated PDF of the phase offset. Systems may comprise processors suitably configured for carrying out the methods of the invention.

Figure 3:
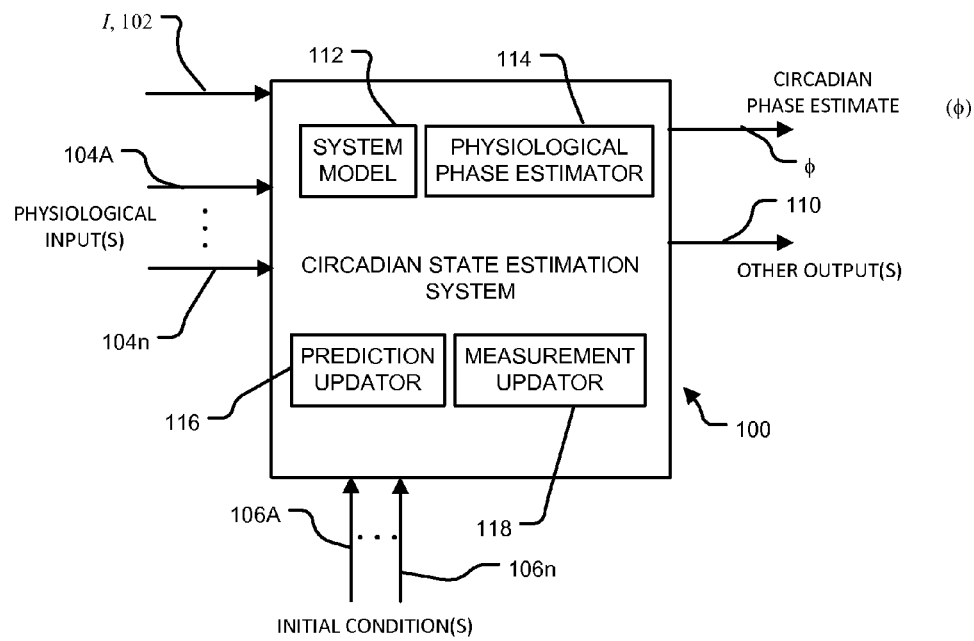
FIG. 3 is a schematic illustration of a system for estimating a belief in a circadian phase according to a particular embodiment of the invention.

FIG. 3 schematically depicts a circadian phase estimation system 100 according to a particular embodiment of the invention. System 100 estimates the circadian phase ϕ of an individual subject (not shown). In particular embodiments, the circadian phase ϕ estimates output by system 100 may comprise statistical information relating to the circadian phase ϕ—e.g. a probability distribution function (PDF) relating to the circadian phase ϕ. Such statistical information may express a belief or confidence interval in the circadian phase ϕ estimate.

In the illustrated embodiment, estimation system 100 receives light input information 102 (also referred to in the drawings as light input information I) which relates to the amount of light experienced by the individual subject. Light information 102, I may be measured and/or controlled. Examples of light sensor input devices (not explicitly shown) which directly measure light to provide light information 102, I include, by way of non-limiting example: illumination sensor(s) which may be located on the body of the subject (e.g. on a wrist-watch, wrist-mounted actigraph or attached to the user's clothing) or which may be located in the environment(s) (e.g. a building or ambient light location) in which the subject is located; and/or the like. Light (illumination) sensors may measure a single spectrum of light wavelengths, or may measure different light spectrum bands with different sensors. Light information 102, I may also come from light estimation devices which estimate an amount of light exposure of the subject based on other criteria. Examples of light estimate devices which estimate light indirectly from another source include, by way of non-limiting example: activity sensors (e.g. a wrist-mounted actigraph or actigraph otherwise connected to the subject) from which sleep (dark) and wake (light) periods may be inferred; a sleep diary in which sleep and wake periods are recorded; a GPS which may be used to determine sunrise and sunset times or the like; a clock which may be used to determine sunrise and sunset times for a particular location; an electrical light control signal which may be indicative of a a time that the light is on and a time that the light is off; and/or the like. Light levels that are inferred may be estimated based in part on ambient outdoor light (e.g. calculated based on latitude, longitude, and time of day) and anticipated indoor light levels, and anticipated location/environment that the subject will be.

System 100 may also receive one or more optional physiological inputs 104A . . . 104n (collectively, physiological inputs 104). Physiological inputs 104 may be related to measurable physiological parameters. Physiological inputs 104 may comprise statistical information relating to the measurable physiological parameters—e.g. PDFs relating to the physiological parameters. In the illustrated embodiment, system 100 also receives one or more optional initial conditions 106A ... 106n (collectively, initial conditions 106). Initial conditions 106 may be estimated or measured. Initial conditions 106 may relate to model variables of a system model (not shown) used by estimation system 100. In addition to the circadian phase φ, estimation system may also output one or more optional other output(s) 110. Such other outputs 110 may be related to the model variables of the system model used by estimation system 100.

In the illustrated embodiment, estimation system 100 comprises a number of components, which include a system model 112, a physiological phase estimator 114, a prediction updator 116 and a measurement updator 118. For simplicity of the schematic illustration, system model 112, physiological phase estimator 114, prediction updator 116 and measurement updator 118 are shown as separate components. However, it will be appreciated by those skilled in the art that these components of estimation system 100 may overlap one another in whole or in part. Physiological phase estimator 114, prediction updator 116 and measurement updator 118 may be implemented, at least in part, using a computer or other suitably configured processor. System model 112, physiological phase estimator 114, prediction updator 116 and measurement updator 118 are explained in more detail below.

Estimation system 100 may be implemented at least in part by one or more suitably configured controllers. In general, the type of controller used to implement system 100 may comprise or may otherwise be embodied by a wide variety of components. For example, such a controller may comprise one or more programmable processor(s) which may include, without limitation, embedded microprocessors, dedicated computers, groups of data processors or the like. Some functions of such a controller may be implemented in software, while others may be implemented with one or more hardware devices. The operation of such a controller may be governed by appropriate firmware/code residing and/or executing therein, as is well known in the art. Such a controller may comprise memory or have access to external memory.

The invention may also comprise methods of operating estimation system 100 to generate estimates of the circadian phase φ.

Modified Kronauer-Jewett Model

Model 112 of estimation system 100 (FIG. 3) may be implemented using a modified version of the Kronauer-Jewett model 10.

Figure 2:
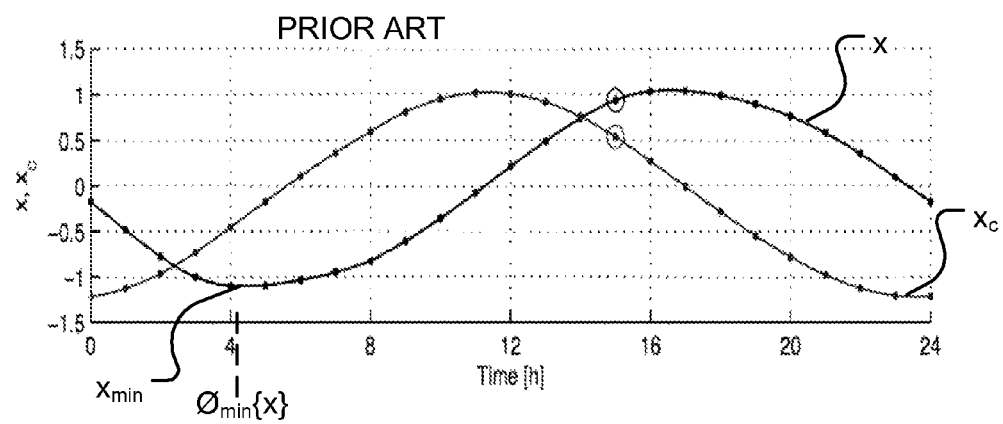
FIG. 2 depicts typical curves of the model variables (x, $x_c$) of the FIG. 1 Kronauer-Jewett model.

As discussed above, the prior art Kronauer-Jewett model 10 (FIG. 1) involves predicting the impact of light exposure I on the circadian parameters of an individual. The Kronauer-Jewett model 10 incorporates a modified Van der Pol oscillator which maintains a steady state oscillation with a stable amplitude and period and models the self-sustaining rhythm of circadian pacemaker 12. A light input term (B) may be incorporated into the oscillator to describe how light intensity I observed in the subject's retina causes changes in the circadian parameters (e.g. phase and/or amplitude). In particular embodiments, the modified Van der Pol oscillator of Kronauer-Jewett model 10 may be described by a pair of interacting model variables (x, $x_c$) described by the following non-linear equations:

$$\dot{x} = \frac{\pi}{12}\left[x_c + \mu\left(\frac{1}{3}x + \frac{4}{3}x^3 - \frac{256}{106}x^7\right) + B\right] \quad (1)$$

$$\dot{x}_c = \frac{\pi}{12}\left[qBx_c - \left[\left[\frac{24}{\tau_x(0.99729)}\right]^2 + kB\right]x\right] \quad (2)$$

where $\mu=0.13$, $q=\frac{1}{3}$, $\tau_x=24.2$, $k=0.55$, and B is a driving input due to light input I (Jewett 1999b). As shown in FIG. 2, the Kronauer-Jewett model variables x and $x_c$ typically follow trajectories which have shapes that are approximately sinusoidal with phases that differ by 90°.

In the Kronauer-Jewett model 10, the response (α) of the human eye to light may be modeled first by a logarithmic function:

$$\alpha = \alpha_0\left(\frac{I}{9500}\right)^p \quad (3)$$

where I is the ambient light intensity in units of lux, $\alpha_0=0.05$ and p=0.5 (Jewett 1999b).

A second component of the Kronauer-Jewett model 10 is a dynamic filter which relates the parameter α to the driving light-input variable (B) used in model variable equations (1) and (2). In accordance with the Kronauer-Jewett model 10, this dynamic filter may be provided by:

$$\dot{n}=60[\alpha(1-n)-\beta n] \quad (4)$$

$$B=G\alpha(1-n)(1-mx)(1-mx_c) \quad (5)$$

where $\beta=0.0075$ and $G=19.875$ (Jewett 1999b). Equation (4) models a filter (n) acting upon (α) and equation (5) models the modulation of the light-input variable (B) by the current model variables (x, $x_c$) of the circadian pacemaker and the filter (n).

The Kronauer-Jewett model 10 also comprises a physiological circadian phase marker 14 which, as discussed above, provides an estimate of the time $\phi_{min}\{CBT\}$ of the subject's minimum core body temperature $CBT_{min}$. In accordance with the Kronauer-Jewett model 10, the estimated time $\phi_{min}\{CBT\}$ of the subject's minimum core body temperature $CBT_{min}$ is based on the corresponding time $\phi_{min}\{x\}$ of the minimum (nadir) $x_{min}$ of the model variable x. More particularly, as shown by summing junction 16 in FIG. 1, the estimated time $\phi_{min}\{CBT\}$ of the subject's minimum core body temperature $CBT_{min}$ is obtained from the corresponding time $\phi_{min}\{x\}$ of the model variable minimum $x_{min}$ according to:

$$\phi_{min}\{CBT\}=\phi_{min}\{x\}+0.8 \text{ hours} \quad (6)$$

Figure 4:
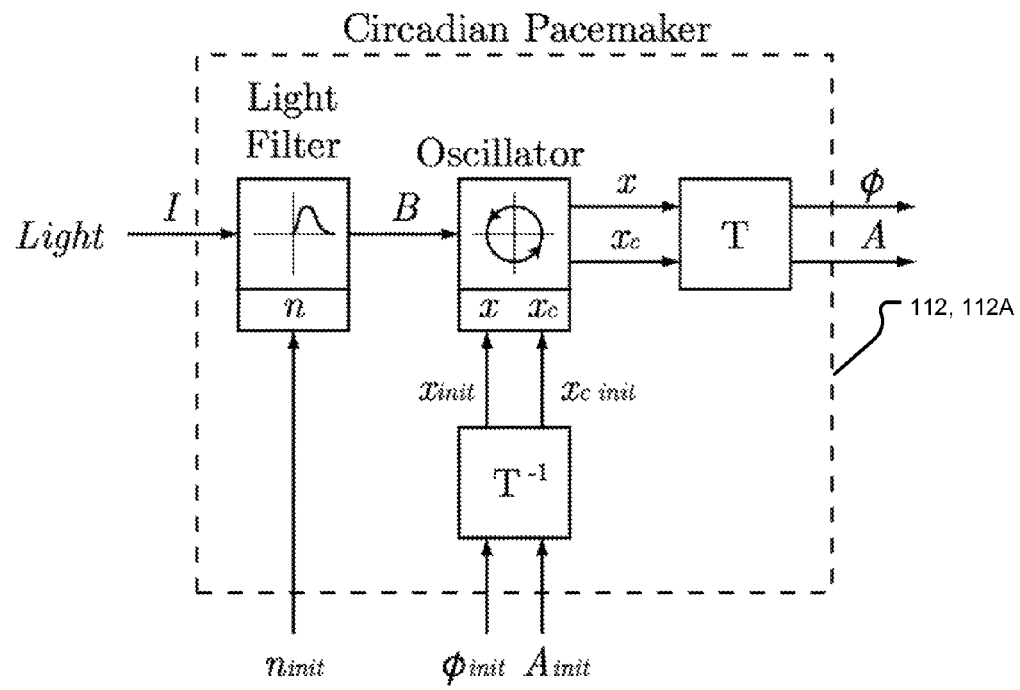
FIG. 4 schematically illustrates a system model which incorporates a modified version of the FIG. 1 Kronauer-Jewett model and which is suitable for use in the FIG. 3 circadian phase estimation system.

System model 112 of estimation system 100 (FIG. 3) may be implemented using the modified version of the prior art Kronauer-Jewett model 10. FIG. 4 schematically depicts a modified Kronauer-Jewett model 112A which may be used to implement system model 112 (FIG. 3) in particular embodiments. In particular embodiments, modified Kronauer-Jewett model 112A (FIG. 4) involves modifying the prior art Kronauer-Jewett model 10 (FIG. 1) by: applying non-linear transformation to circadian pacemaker 12 of the prior art Kronauer-Jewett model 10 (FIG. 1); modifying physiological marker 14 of the prior art Kronauer-Jewett model 10 to provide a physiological phase estimator 114 (FIG. 3) capable of accommodating probability distributions (rather than point estimates) and capable of optionally relating the output of model 112 to multiple physiological inputs 104 which may include physiological inputs other than CBT. Modified Kronauer-Jewett model 112A is explained in more detail below.

Parameter Transformation of Circadian Pacemaker Model

The Kronauer-Jewett model 10 is a widely accepted characterization of a subject's circadian state and the responsiveness of the circadian state to light inputs. The Kronauer-Jewett model 10 suffers from the fact that phase and amplitude of the subject's circadian state are not accessible as model variables. Instead, the Kronauer-Jewett model 10 requires that the circadian amplitude be defined as a nonlinear function of the model variables (x, $x_c$) and the circadian phase be defined by physiological marker component 14 in relation to the nadir $x_{min}$ of the model variable x. As a consequence of these definitions, the location of the nadir $x_{min}$ of the model variable x provides the reference point for connecting the circadian phase predicted by the Kronauer-Jewett model 10 to the circadian phase observable from measurement of the subject's CBT as described above in equation (6).

In accordance with particular embodiments of the invention, this limitation of the prior art Kronauer-Jewett model 10 may be overcome by providing modified Kronauer-Jewett model 112A (FIG. 4) with a transformation T which maps the Kronauer-Jewett model variables (x, $x_c$) into directly useful model variables ($\phi$, A). Modified Kronauer-Jewett model 112A of FIG. 4 may be more fully understood by examining the properties of the Kronauer-Jewett model variables (x, $x_c$) and deriving the transformation T and its inverse transformation $T^{-1}$.

Characteristics of Kronauer-Jewett Model Variables (x, $x_c$)

The differential equations (1), (2), (4) used in the Kronauer-Jewett model 10 comprise three model variables (x, $x_c$, n). As discussed above, the model variables (x, $x_c$) interact to create a modified Van der Pol oscillator which self-oscillates at a period of approximately 24 hours. Both x and $x_c$ follow nearly sinusoidal trajectories, in which the phase of the model variable $x_c$ lags the phase of the model variable x by approximately 90°. The model variable n is part of a light input system.

In an approximately 24 hour period of the model variables (x, $x_c$), the prior art Kronauer-Jewett model 10 uses a single reference point (i.e. the time $\phi_{min}\{x\}$ of the nadir $x_{min}$ of the model variable x) to define the phase of the circadian pacemaker. For example, for an individual with sleep occurring regularly between 12:00 am and 8:00 am, simulations of the Kronauer-Jewett model 10 will tend to show that the nadir $x_{min}$ of the model variable x occurs at a time $\phi_{min}\{x\}$ around 4.3 h (4:22 am), and in real experiments subjects will have a CBT minimum $CBT_{min}$ occurring at a time $\phi_{min}\{CBT\}$ of approximately 5.1 h (5:06 am) as described above in equation (6). Based on a variety of experiments with different light exposure settings, the Kronauer-Jewett model 10 has been refined so that the time $\phi_{min}\{x\}$ of the nadir $x_{min}$ maintains a constant time shift (0.8 hours) relative to the time $\phi_{min}\{CBT\}$ observed for the CBT nadir $CBT_{min}$.

Figure 1:
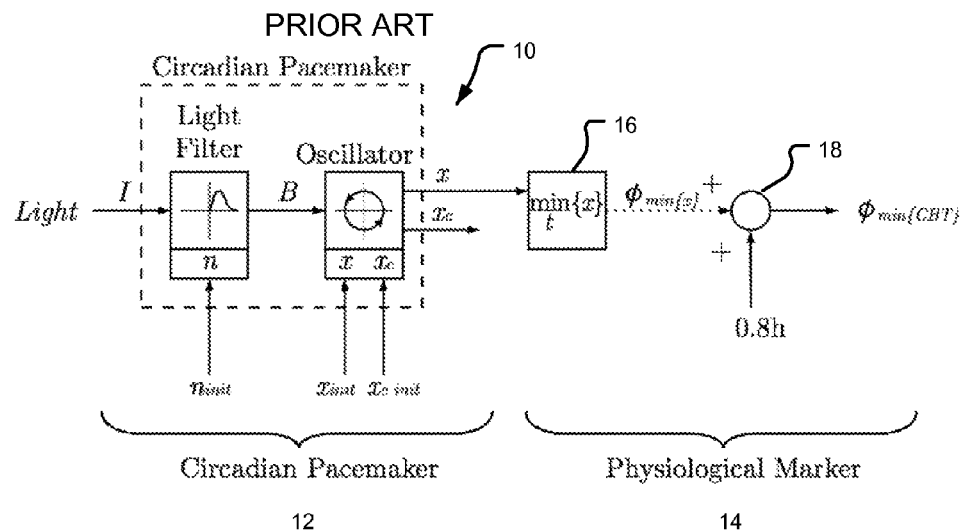
FIG. 1 schematically depicts the prior art Kronauer-Jewett model for circadian phase estimation in response to changes in light exposure.

This nadir-phase-reference method of the Kronauer-Jewett model 10 presents a number of limitations in the context of a circadian estimation system 100 (FIG. 3). Firstly, the Kronauer-Jewett model 10 only outputs one phase prediction every approximately 24 hours—i.e. one time $\phi_{min}\{x\}$ in the FIG. 1 illustration corresponding to each nadir $x_{min}$ of the model variable x. This single phase prediction permits only one physiological marker output (i.e. one time $\phi_{min}\{CBT\}$ in the FIG. 1 illustration) every approximately 24 hours. A second limitation of the Kronauer-Jewett nadir-phase-reference method relates to the lack of an inverse relationship from which the system's model variables (x, $x_c$, n) can be updated to match a given circadian phase and amplitude. Typically, in prior art applications, the initial conditions for Kronauer-Jewett simulations are assigned on the basis of a look-up table of values for typical situations (e.g. for a habitual schedule of 8 h sleep and 16 h awake in 160 lux the initial conditions at the onset of sleep time may be set to x=−0.17, $x_c$=−1.22, and n=0.50 (Jewett 1999b)).

Parameter Transformation to New Model Variables ($\phi$, A)

Figure 5:
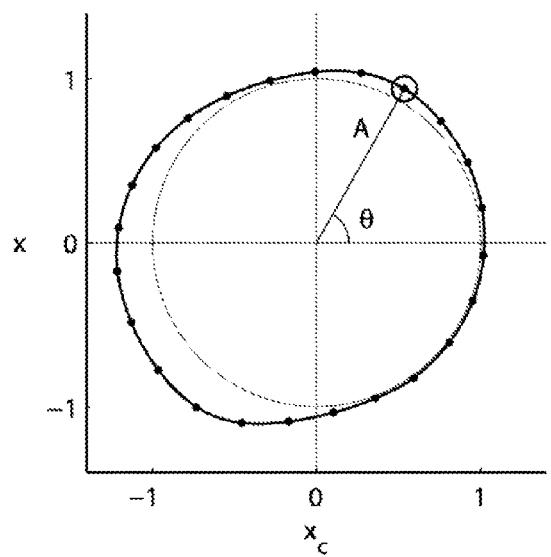
FIG. 5 is a graphical relationship between the model variables (x, $x_c$) of the FIG. 1 Kronauer-Jewett model and the model variables (A, $\phi$) of the FIG. 4 modified Kronauer-Jewett model.

In particular embodiments of the invention, the modified Kronauer-Jewett model 112A (FIG. 4) comprises a transformation T for creating new phase and amplitude model variables ($\phi$, A) based on Kronauer-Jewett model variables (x, $x_c$). Since Kronauer-Jewett model variables (x, $x_c$) are continuously updated (e.g. once every time step in a discrete-time context), the transformed phase and amplitude model variables ($\phi$, A) of modified Kronauer-Jewett model 112A are similarly continuously updated. Transformation T may be based on an understanding of the Kronauer-Jewett model variables (x, $x_c$). As shown in FIG. 1, the Kronauer-Jewett model variables (x, $x_c$) typically follow near-sinusoidal trajectories with a relatively constant phase difference. If the Kronauer-Jewett model variables (x, $x_c$) are considered to be (x, y) coordinates on a Cartesian plane, then they describe a near-circular locus. FIG. 5 shows the FIG. 2 data points transposed into (x, y) coordinates. The near-circular (x, y) plot shown in FIG. 5 may be described in a polar coordinate system using amplitude A and phase angle $\theta$, where the amplitude A is the distance of the vector from the origin to the point (x, $x_c$) and the angle $\theta$ is measured from the horizontal axis as shown in FIG. 5. The Kronauer-Jewett model variables (x, $x_c$) may be transformed to provide the amplitude A and the phase angle $\theta$ according to:

$$A = \sqrt{x^2 + x_c^2} \tag{7}$$

$$\theta = \tan^{-1}\left(\frac{x}{x_c}\right) + \begin{cases} 0 & \text{if } x_c > 0 \text{ and } x > 0 \text{(quadrant I)}, \\ \pi & \text{if } x_c < 0 \text{(quadrant II or III)}, \\ 2\pi & \text{if } x_c > 0 \text{ and } x < 0 \text{(quadrant IV)}, \end{cases} \tag{8}$$

With these definitions, as time increases the point (x, $x_c$) follows a near-circular trajectory with a period of 24 hours and the angle $\theta$ increases from 0 to $2\pi$ radians. Together, equations (7) and (8) may be defined to be a transform T. The inverse transform $T^{-1}$ may be accomplished according to:

$$x = A \sin(\theta) \tag{9}$$

$$x_c = A \cos(\theta) \tag{10}$$

In practice, it is most meaningful to describe the circadian system in terms of a phase offset $\phi$ which reflects the phase shift relative to a defined reference phase, rather than in terms of a phase angle $\theta$ which reflects the continually moving angle from 0 to $2\pi$. The following relationship may be used to define the phase offset $\phi$ (in units of hours) based on the phase angle $\theta$:

$$\theta = \omega(t + t_0) - \phi \frac{2\pi}{24} \tag{11a}$$

or $$\phi = \frac{24}{2\pi}(\omega(t + t_0) - \theta) \tag{11b}$$

where $\omega$ represents a baseline frequency, $t_0$ is a baseline offset parameter measured in hours from midnight (i.e. midnight=0 hours) and t represents the current time measured in hours from midnight. Since the baseline frequency ω corresponds to a constant 24 hour day (i.e. ω=2π/24), equation (11) can be rewritten as:

$$\phi = t + t_0 - \frac{24}{2\pi}\theta \quad (12)$$

In accordance with the definition of the phase offset φ in equation (11) and (12), the phase offset φ represents the difference between the phase angle term 24θ/2π and time variable t in units of hours.

Figure 6A:
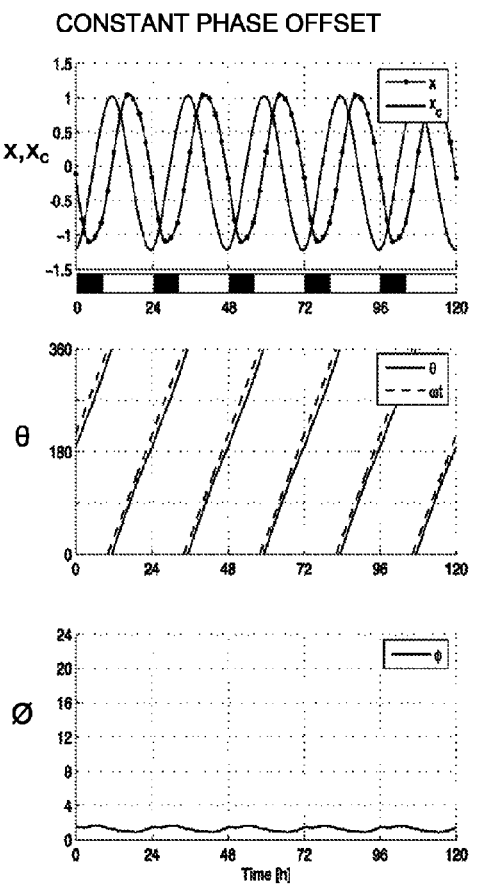
FIGS. 6A and 6B respectively depict plots showing the phase angle θ and the phase offset ϕ for the cases of a constant phase offset ϕ and for the case of a shift in phase offset ϕ.
Figure 6B:
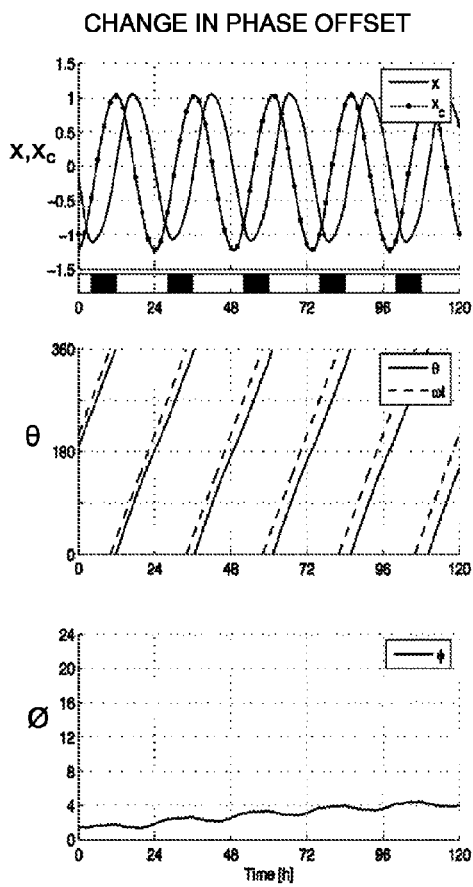

Referring to equation (12), if an individual follows a consistent 24 light exposure schedule, then the time t will vary between 0 hours and 24 hours and the phase angle θ will vary between 0 and 2π over the same period. This situation is depicted in the plots of FIG. 6A. Because of the corresponding changes in time t and phase angle θ over a period, the term will increase at the same rate as t, so the difference will be relatively constant. This constant phase offset φ is shown in the lower plot of FIG. 6A. Alternatively, if an individual experiences a shift in light exposure (as is shown in the plots of FIG. 6B), then the phase angle θ will vary by a different amount over a 24 hour period—i.e. an amount different than 0 to 2π. Consequently, the term of equation (12) will increase or decrease relative to the time t and a change in the phase offset φ will occur. In the circumstance shown in the lower plot of FIG. 6B, the phase offset φ is increasing.

The equation (12) baseline offset term $t_0$ may be treated as a calibration constant, as it shifts the mean value of the phase offset φ. In particular embodiments, to determine the appropriate calibration value $t_0$, a comparison is made between the phase offset φ estimated using equation (12) and the transformation T (FIG. 4 and equations (7) and (8)) to the phase offset φ estimated using the Kronauer-Jewett nadir-reference method described above. For consistency, the phase offset φ of the modified model (i.e. estimated using equation (12)) may be calibrated to match the phase offset φ estimated using the Kronauer-Jewett nadir-reference method. Since the Kronauer-Jewett nadir-phase-reference method provides only a single reference point every approximately 24 hours (i.e. at the nadir $x_{min}$ of the model variable x) and the phase offset φ estimated using equation (12) provides continuous values, a variety of calibration methods may be used to select the baseline offset term $t_0$.

In one particular embodiment, calibration involves adjusting the baseline offset term $t_0$, such that the 24 hour mean of the equation (12) phase offset estimate φ matches the phase estimate φ at the time of $x_{min}$ predicted using the Kronauer-Jewett nadir-reference method—i.e. if the time of $x_{min}$ occurs at 4:00 h, then $t_0$ is chosen such that the 24 hour mean of the equation (12) phase offset estimate φ will equal 4:00 h. In an alternative embodiment, calibration involves adjusting the baseline offset term $t_0$ of the equation (12) phase offset estimate φ such that the values of the equation (12) phase offset estimate φ exactly match the phase estimates φ predicted by the Kronauer-Jewett nadir-reference method at the reference points corresponding to the nadir $x_{min}$ of the model variable x. In the description that follows, unless otherwise stated, it is assumed that the calibration technique of matching the mean of the equation (12) phase estimate φ is used to obtain the baseline offset term $t_0$.

Using the 24 hour mean of the equation (12) phase offset φ, a specific calibration value for the baseline offset term $t_0$ was determined from a simulation of modified Kronauer-Jewett model 112A (FIG. 4) under conditions which are considered to involve a standard sleep schedule and light exposure scenario. More particularly, the simulation involved repeated days comprising an eight hour sleep episode (at a light level of 0 Lux) followed by a sixteen hour awake episode (at a constant light level of 150 Lux) until modified Kronauer-Jewett model 112A achieved steady state conditions. In accordance with this simulation, the value of $t_0$ which causes the mean of the equation (12) phase offset estimate φ to match the phase offset estimates φ predicted using the Kronauer-Jewett nadir-reference method was determined to be $t_0$=17.1 hours. Accordingly, the resulting calibrated version of equation (12) may be rewritten as:

$$\phi = t + 17.1 - \frac{24}{2\pi}\theta \quad (13)$$

where θ is given by equation (8). Phase offset estimates φ based on equation (12) and/or equation (13) may be referred to herein as phase offset estimates φ obtained using continuous phase estimation in contrast to phase offset estimates φ obtained using the Kronauer-Jewett nadir-reference method. In addition, unless specifically stated otherwise, references in the remainder of this description to phase should be understood to refer to phase offset φ—i.e. the word offset may be dropped without loss of generality.

Figure 7A:
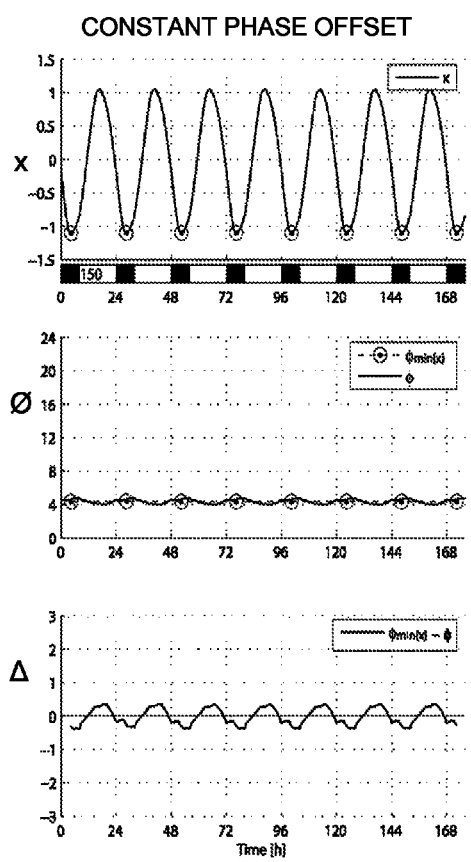
FIGS. 7A and 7B respectively depict plots showing how the continuous phase offset estimates compare to the Kronauer-Jewett nadir-reference phase offset estimates for the case where the phase offset is relatively constant (i.e. where a subject has entrained to particular pattern of sleep and light exposure) and for the case of a shift in phase offset.
Figure 7B:
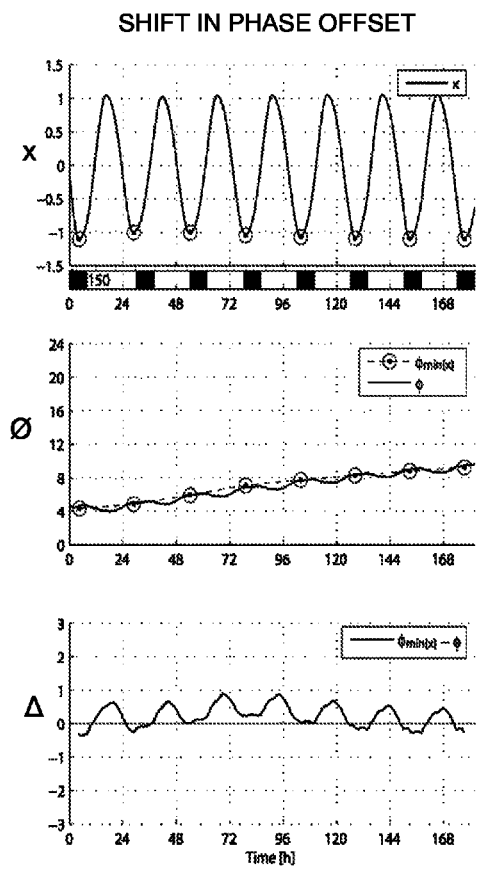

FIGS. 7A and 7B respectively depict plots showing how the continuous phase estimates compare to the Kronauer-Jewett nadir-reference phase estimates for the case where the phase is relatively constant (i.e. where a subject has entrained to particular pattern of sleep and light exposure) and for the case of a phase shift. In each of FIGS. 7A and 7B: the upper plots represent the model variable x and the circled points in the upper plots represent the nadirs $x_{min}$ of the model variable x; the middle plots represent the continuous phase estimates φ and the circled points in the middle plots represent the phase estimates φ obtained using Kronauer-Jewett nadir-reference method at the nadirs $x_{min}$ of the model variable x; and the lower plots represent a difference Δ between the continuous phase estimates φ and the circled points in the middle plots represent the phase estimates φ obtained using Kronauer-Jewett nadir-reference method.

FIG. 7A shows that Δ fluctuates within each 24 hour period (due to the fact that the Van der Pol equations (1) and (2) are not perfectly sinusoidal) but that Δ is less than about ±0.5 hours for the case of entrained phase offset. The amplitude of this fluctuation is considered sufficiently small to obtain reasonably accurate phase estimates as explained in more detail below. In the plots of FIG. 7B, the individual's sleep pattern is delayed by six hours from the entrained rhythm. This results in a six hour shift in the circadian phase φ as shown in the middle FIG. 7B plot. The lower FIG. 7B plot shows that Δ exhibits a small positive bias during phase transition, but that this bias disappears once the phase φ entrains to its new value. This bias is a transient effect which does not significantly impact phase estimates.

Referring back to modified Kronauer-Jewett model 112A of FIG. 4, it may be observed that modified Kronauer-Jewett model 112A incorporates a transform component T which transforms the Kronauer-Jewett model variables (x, $x_c$) into transformed model variables (A, φ). In the above-described embodiment, transform component T may be implemented using equation (9) and one of equations (12) or (13). Modified Kronauer-Jewett model 112A also comprises an inverse transform component $T^1$ which transforms initial conditions ($\Delta_{init}$, $\phi_{init}$) into Kronauer-Jewett initial conditions ($x_{init}$, $x_{c\_init}$). In the above-described embodiment, inverse transform component T' may be implemented using equations (9) and (10).

State-Space Model

It is convenient, but not necessary, for the purposes of the Bayesian estimation methods described below to re-cast the modified Kronauer-Jewett model 112A into a state-space form. State-space models are defined by a state vector x that contains the time varying properties (e.g. time-varying model variables) of the system, a state transition function (also referred to as a state propagation function) that describes how the state vector evolves in time, and an output function that describes how the model variables can be observed. We may define a state vector x which includes the three model variables of the modified Kronauer-Jewett model 112A:

$$x = \begin{bmatrix} A \\ \phi \\ n \end{bmatrix} \quad (14)$$

where A is circadian amplitude, $\phi$ is circadian phase, and n is the light filter state. For the case of a discrete-time system, the state vector x and its model variables (which may be referred to as the states of the state-space model) evolve at incremental time intervals (also referred to as time steps) with sampling period T. This discrete-time formulation may be described according to:

$$x_k = x(t) \text{ where } t = t_0 + kT, k \in N \quad (15)$$

In addition to the state vector x, state-space models comprise a state transition function and an output function. For discrete-time systems, the general state transition function may be written:

$$x_{k+1} = f(x_k, u_k, v_k) \quad (16)$$

where $x_k$ is the current state vector at time step k, $u_k$ is a measured input, $v_k$ is an unmeasured input, and $x_{k+1}$ is the predicted state vector at the future time step k+1. The unmeasured input $v_k$ is often referred to as process noise and may be modeled as a random variable. To cast the modified Kronauer-Jewett model 112A in the form of equation (16), it may be observed from FIG. 4 that model 112A describes a state transition function $x_{k+1} = f_k(x_k, I_k)$ where I is the light input and $x_k$ is given by equation (14). The FIG. 4 model 112A does not contain a process noise term $v_k$, as a state-space formulation of modified Kronauer-Jewett model 112A has not previously been developed. Particular embodiments of the invention involve the assumption that the process noise $v_k$ is an additive Gaussian noise. In other embodiments, other forms of PDFs (e.g. uniform probability PDFs) may be used to model the process noise $v_k$. With the assumption that the process noise $v_k$ is an additive Gaussian noise, the state-space transition equation for the modified Kronauer-Jewett model 112A may be expressed in the following form:

$$x_{k+1} = f(x_k, I_k) + v_k \quad (17)$$

$$\begin{bmatrix} A \\ \phi \\ n \end{bmatrix}_{k+1} = \begin{bmatrix} f_1(x_k, I_k) \\ f_2(x_k, I_k) \\ f_3(x_k, I_k) \end{bmatrix} + \begin{bmatrix} v1 \\ v2 \\ v3 \end{bmatrix}$$

The general form of the discrete-time state-space output function is:

$$z_k = h_k(x_k, w_k) \quad (18)$$

where w is a random variable referred to as the measurement noise. An output function for the modified Kronauer-Jewett model 112A may be chosen based on the model variables to which measurement information could potentially be correlated. Of the three model variables, A, $\phi$, and n, the phase $\phi$ may be observed using physiological markers as described above. Accordingly, in particular embodiments, the phase $\phi$ may be chosen as the single output of interest. In such embodiments, the phase $\phi$ may be extracted using the following linear output function:

$$\begin{aligned} z &= h_k(x_k, w_k) \\ &= Hx_k + w_k \\ &= [0\,1\,0] \begin{bmatrix} A \\ \phi \\ n \end{bmatrix} + w_k \\ &= [\phi] + w_k \end{aligned} \quad (19)$$

In particular embodiments, the measurement noise $w_k$ may be selected to be an independent random Gaussian variable with variance R. In other embodiments, the measurement noise $w_k$ may be assumed to have other PDFs. It will be appreciated that the output function (19) could be modified if other quantities (e.g. circadian amplitude A) were of interest.

Incorporating Inputs with Probability Distributions

Particular embodiments of the invention provide the ability to measure one or more physiological systems of the subject to provide physiological inputs 104 (FIG. 3). Such physiological inputs 104 may include CBT, but may additionally or alternatively include other physiological inputs, such as, by way of non-limiting example: hormonal melatonin concentration, hormonal cortisol concentration, rate of cell proliferation, the cardiac regulatory system, chemoreceptive respiratory feedback system, sleep/wake schedules, physical activity levels and cognitive performance (alertness). Sleep/wake schedules may be maintained in a sleep log, for example. Physical activity levels may be monitored by a suitable sensor such as a wrist-mounted actigraph, another type of actigraph or the like. Physiological phase estimator 114 (FIG. 3) may receive physiological inputs 104 and may use such inputs 104 to provide physiological markers of the circadian phase $\phi$ as described in more detail below. A non-limiting example of a physiological marker which may be inferred from sleep/wake schedules and/or activity levels is a time of habitual waking. It is desirable, in some embodiments, to integrate these physiological inputs 104 into to a common circadian phase domain. In the illustrated embodiment of phase estimating system 100 (FIG. 3), physiological phase estimator 114 uses measured physiological inputs 104 to generate corresponding statistical PDFs relating to the phase marker(s) in the circadian phase domain.

Figure 8:
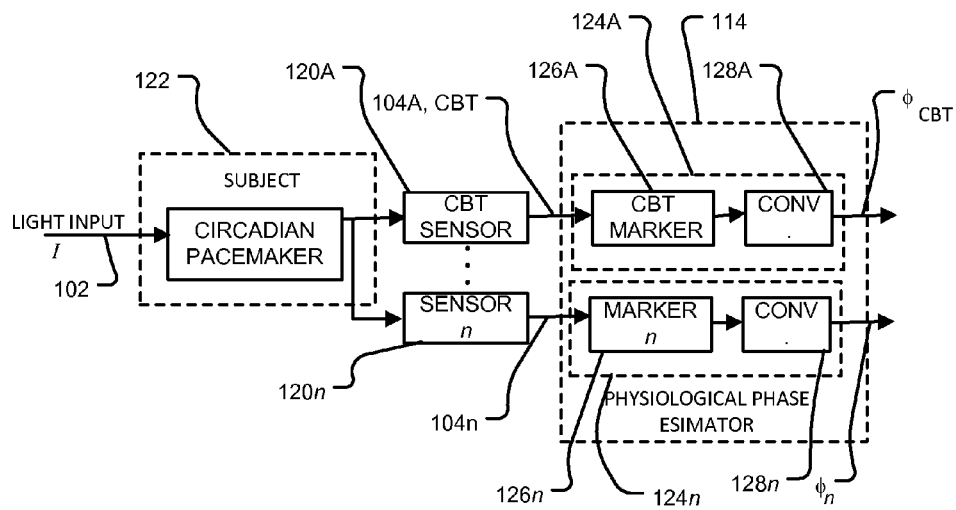
FIG. 8 a schematic depiction of the operation of the physiological phase estimator of the FIG. 1 system according to a particular embodiment of the invention.

FIG. 8 is a schematic depiction of the operation of physiological phase estimator 114 according to a particular embodiment of the invention. In the illustrated embodiment of FIG. 8, several sensors 120A, . . . 120n (collectively, sensors 120) are configured to sense physiological phenomena of subject 122. Such physiological phenomena may include, by way of non-limiting example, CBT, hormonal melatonin concentration, hormonal cortisol concentration, rate of cell proliferation, the cardiac regulatory system, chemoreceptive respiratory feedback system, sleep/wake schedules, physical activity levels, and cognitive performance (alertness). In the illustrated embodiment, sensor 120A senses the CBT of subject 122 and at least one other sensor 120n is provided to detect another physiological phenomena of subject 122. The outputs of sensors 120 are the physiological inputs 104 (see also FIG. 3). In the illustrated embodiment of FIG. 8, sensor 120A outputs a physiological input 104A representative of the CBT of subject 122 and sensor 120n outputs a physiological input 104n representative of another physiological phenomena of subject 122.

Physiological inputs 104 are provided to physiological phase estimator 114. For each of physiological inputs 104, physiological phase estimator 114 comprises a component phase estimator 124A, . . . 124n (collectively, component phase estimators 124). Component phase estimators 124 comprise marker components 126A, . . . 126n (collectively, marker components 126) and marker-to-phase converter components 128A, . . . 128n (collectively, marker-to-phase converter components 128). Marker components 126 perform the function of extracting features from their physiological inputs 104. The features extracted by marker components 126 comprise physiological markers indicative of the circadian phase of subject 122. While the features extracted by marker components 126 may generally comprise any discernable features of inputs 104, non-limiting examples of features which may be extracted by marker components comprise: local minima or maxima of inputs 104, the presence of inputs 104 above and/or below a threshold, frequencies of inputs 104, rates of change (i.e. time derivatives) of inputs 104, time integrals of inputs 104 and/or any similar features of the rate of change or time integral of inputs 104. In particular embodiments, marker components 126 may also extract the time associated with any extracted features.

The features extracted by marker components 126 are preferably associated with PDFs representing the uncertainty present in the accuracy of the feature extraction. In particular embodiments, such physiological feature PDFs may comprise Gaussian PDFs characterized by a mean value and a standard deviation. In other embodiments, the physiological feature PDFs may comprise other distributions characterized by other parameters. In the case of CBT, the feature extracted by marker component 126A is the CBT minimum ($CBT_{min}$) and marker component 126A may also extract the corresponding time associated with $CBT_{min}$. In the above discussion (see FIG. 1), the time associated with $CBT_{min}$ is referred to as $\phi_{min}\{CBT\}$. A PDF associated with the time $\phi_{min}\{CBT\}$ at which $CBT_{min}$ occurs may be obtained in accordance with the procedure outlined by E. Brown and C. Czeisler, The statistical analysis of circadian phase and amplitude in constant-routine core-temperature data, Journal of Biological Rhythms, 7:3, 177-202; 1992.

Figure 25:
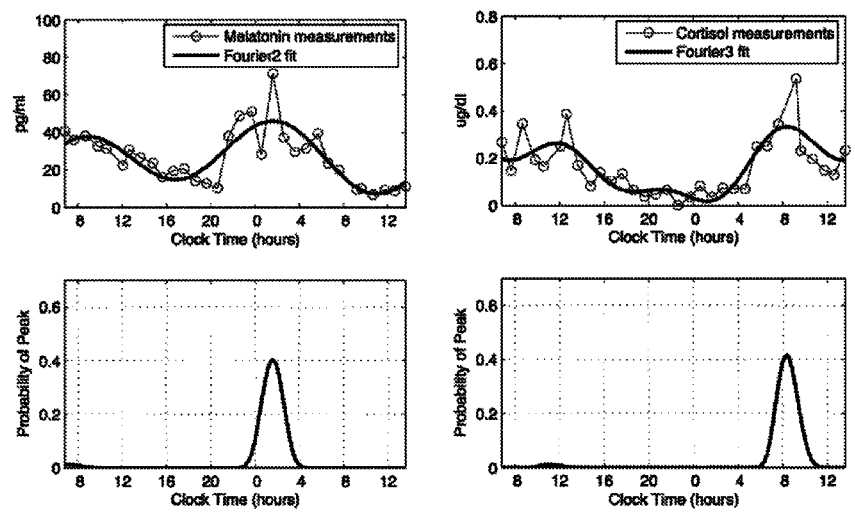
FIG. 25 shows melatonin and cortisol measurements taken from an individual subject and shows the results of a Fourier curve-fitting technique used to obtain physiological feature PDFs according to a particular embodiment of the invention.

Marker components 126 may also determine physiological feature PDFs from physiological inputs 104n using Fourier series curve-fitting techniques. A suitable second or third order Fourier series curve fitting technique is shown in FIG. 25 in relation to melatonin and cortisol samples taken from an individual during a laboratory study. The phase marker for the melatonin and cortisol examples can be extracted by identifying the time at which the maxima of the fitted curve occurs. A PDF time at which the maxima occurs may be generated and used as the phase PDF. Algorithms such as the procedure outlined by Wang (Y. Wang and M. Brown, A flexible model for human circadian rhythms, Biometrics 52, 588-596; 1996) may be applied.

In the illustrated embodiment, marker-to-phase converter components 128 perform the function of converting the features extracted by marker components 126 and/or their corresponding times into information relating to the circadian phase $\phi$ of subject 122. For example, in the case of CBT, it has been experimentally determined (as discussed above) that the time $\phi_{min}\{CBT\}$ associated with the feature $CBT_{min}$ can be related to the calibrated circadian phase $\phi$ (equation (13)) of subject 122 via a 0.8 hour time/phase shift (note that when phase is described as phase offset $\phi$, its units are units of time and therefore a time shift and a phase shift are equivalent).

While particular embodiments of marker-to-phase converter components 128 may implement time/phase shifting functions (as is the case for CBT converter component 128A), this is not necessary. In other embodiments, marker-to-phase converter components 128 may involve other conversion functions. For example, in the case where a feature extracted by a marker component 126 is not a time/phase quantity, the corresponding marker-to-phase converter component 128 may use the extracted feature as the basis of a function or a transformation or the like to convert the extracted feature into time/phase information relating to the circadian phase $\phi$.

The information relating to circadian phase $\phi$ that is output by marker-to-phase converter components 128 does not necessarily suggest internal physical mechanisms in subject 122, but rather this information provides descriptors of observable physiological behavior. The information relating to circadian phase $\phi$ that is output by marker-to-phase converter components 128 sets the foundation for implementing a recursive state estimation algorithm, which may simultaneously make use of one or more physiological inputs 104 and central state transition updates.

Particle Filter Phase Estimator

The above-described modeling framework describes the dynamics of circadian physiology in a state-space model and optionally integrates multiple physiological inputs 104. In particular embodiments, phase estimator 100 (FIG. 3) uses a particle filter to estimate the circadian state within this modeling framework. In general, it is desired to provide a phase estimation solution that can incorporate statistical process noise (as opposed to an algebraic solution), incremental or on-line processing of information at every time step (as opposed to batch data analysis) and statistical distributions of measurements and parameter estimates (e.g. physiological inputs 104 and the information about circadian phase $\phi$ extracted from physiological inputs by phase estimator 114). Particular embodiments of phase estimator 100 (FIG. 3) involve the use of recursive filtering methods which in turn make use of Bayesian statistics. Such techniques may be referred to Bayesian filtering or Bayesian estimation techniques. A feature of Bayesian estimation is the integration of prediction updates (which may be implemented by prediction updator 116 (FIG. 3)) and measurement updates (which may be implemented by measurement updator 118 (FIG. 1)) using inferential statistics. In particular embodiments, phase estimator 100 (FIG. 3) uses a particle filter as a method for resolving the Bayesian estimation problem.

Overview of Recursive Bayesian Estimation

Bayesian statistics provides an approach to on-line estimation (i.e. estimation at each time step) in which the probability, or belief, of a system's property is updated based on an initial belief, new measurements, and predictions of the system's internal dynamics. A statistical probability is associated with each operation which allows for natural expression of the uncertainty that is inherent in most real systems and allows for analysis of noisy or otherwise imperfect measurements. Applied to discrete-time state-space models, the values of a state vector are estimated starting from a prior probability distribution and sequentially updated with predictions from a state transition equation and adjustments from a measurement equation.

Consider a discrete-time state-space model with a state vector x that is evaluated at times $t_i = iT$, where T is the sampling period. Denoting measurements at time $t_i$ as $z_i$, the set of all measurements up to time k may be defined as $Z_{k-z_i}$, i=1, ..., k. The state-space model consists of a state transition equation:

$$x_k = f_k(x_{k-1}, u_{k-1}, v_{k-1}) \quad (20)$$

which describes the evolution of states from a prior state $x_{k-1}$ to a future state $x_k$ with measured inputs $u_{k-1}$ and noise $v_{k-1}$ and a measurement or output equation:

$$z_k = h_k(x_k, w_k) \quad (21)$$

which describes the relationship between an observed measurement $z_k$ and the system's internal state $x_k$ and the measurement noise $w_k$.

To apply Bayesian statistical logic, both the state transition and measurement equations (20) and (21) are extended to include probability distributions. Assuming a known probability distribution of the states at time $t_{k-1}$ is $p(x_{k-1}|Z_{k-1})$, then the probability distribution of states at a future time step $p(x_k|Z_{k-1})$ is defined by the Chapman-Kolmogorov equation (also referred to as the prediction update equation):

$$p(x_k|Z_{k-1}) = \int_{-\infty}^{\infty} p(x_k|x_{k-1}) p(x_{k-1}|Z_{k-1}) dx_{k-1} \quad (22)$$

The term $p(x_k|x_{k-1})$ expresses the probability distribution of the state vector x at time $t_k$ given a state vector $x_{k-1}$ at time $t_{k-1}$ and is related to the state transition equation (20). Prediction update equation (22), which may be implemented by prediction updator 116 (FIG. 1), therefore allows the belief in the system state vector to evolve in time based on predictions from state transition equation (20). A probabilistic update of states based on measurements is provided by Bayes theorem which states that:

$$p(x_k|Z_k) = \frac{p(z_k|x_k) \cdot p(x_k|Z_{k-1})}{p(z_k|Z_{k-1})} \quad (23)$$

where $p(x_k|Z_{k-1})$ represents the prior knowledge of the states at time $t_k$ given all measurements up to time $t_{k-1}$; $p(z_k|x_k)$ is the likelihood from the current observed data point at time $t_k$; and $p(x_k|Z_k)$ is the posterior probability of the state variables. The denominator $p(z_k|Z_{k-1})$ is a normalization constant. Consequently, equation (23) may be expressed as:

$$p(x_k|Z_k) = C p(z_k|x_k) p(x_k|Z_{k-1}) \quad (24)$$

where C is a normalization constant. Equation (24) may be referred to as the measurement update equation. The measurement update equation (24), which may be implemented by measurement updator 118 (FIG. 1), allows an update of the system's state vector based on new measurements.

Figure 9:
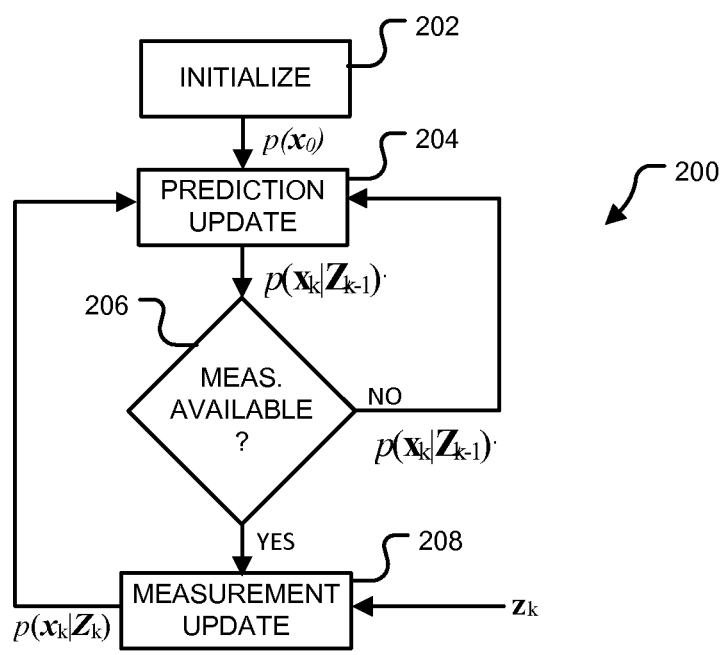
FIG. 9 schematically depicts a method 200 of Bayesian filtering according to a particular embodiment of the invention.

FIG. 9 schematically depicts a method 200 of Bayesian filtering according to a particular embodiment of the invention. Given an initialization of the prior probability distributions of the states $p(x_0)$ obtained in block 202, prediction update equation (22) may be applied in block 204 to obtain a belief (probability distribution) $p(x_k|Z_{k-1})$ in the system state vector. Method 200 then proceeds to block 206 which involves an inquiry into whether there measurement information is available in the current time step. If no measurement information is available (block 206 NO output), then Bayesian filtering method 200 returns to prediction update block 202 for another iteration. If measurement information is available (block 206 YES output), then method 200 proceeds to block 208 where measurement update equation (24) is used to incorporate the measurement information $z_k$ and to generate an updated belief $p(x_k|Z_k)$ in the system state vector. Method 200 then loops back to prediction update block 204. While method 200 of FIG. 9 represents a general sequence of operations for Bayesian filtering, specific implementation of the block 204 prediction update and the block 208 measurement update vary widely however based on the characteristics of the system of interest and on design criteria.

Solving the Circadian State-Spaced Bayesian Filtering Problem

Figure 10:
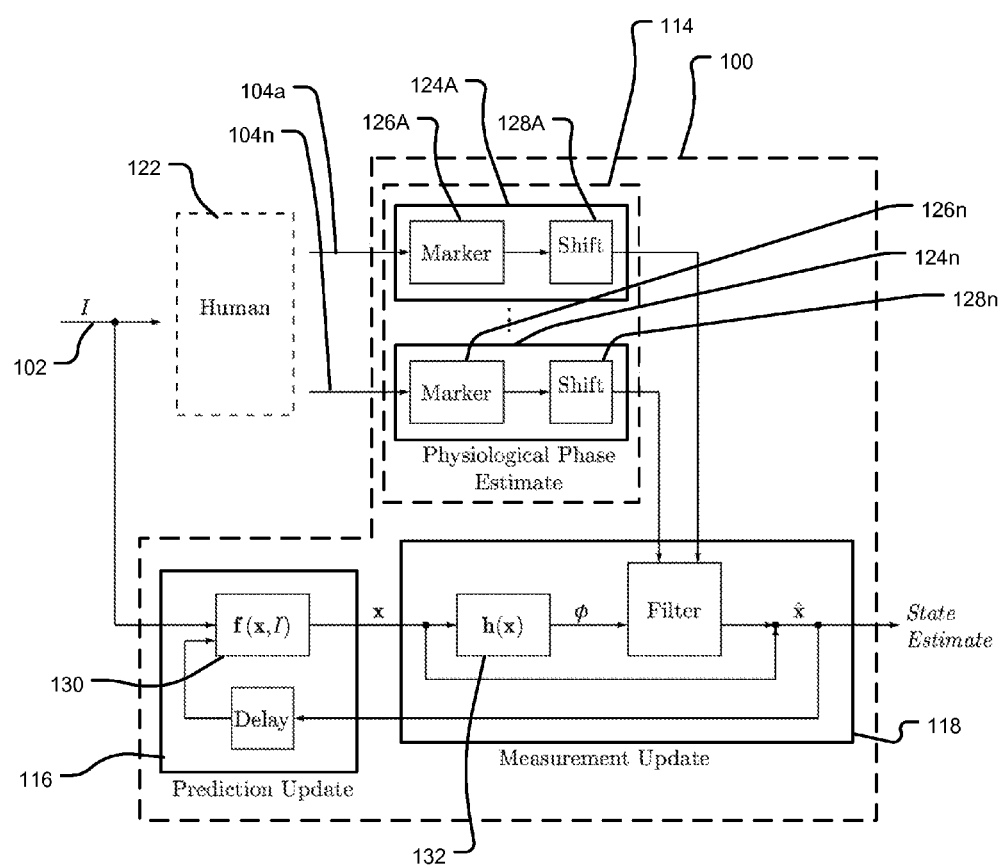
FIG. 10 is a more detailed schematic depiction of the FIG. 1 estimation system.

Particular embodiments of the invention provide methods for solving Bayesian estimation problems applied to the modified Kronauer-Jewett model 112A to generate estimated probabilities/beliefs of the circadian phase φ. FIG. 10 schematically depicts an estimation system 100 which integrates the modified Kronauer-Jewett model 112A, multiple optional physiological inputs 104, initial conditions 106, physiological phase estimator 114, prediction updator component 116 and measurement updator component 118. In the schematic illustration of FIG. 10, modified Kronauer-Jewett model 112A may be incorporated into state transition component 130 (f(x, I)) of prediction updator component 116 and possibly into output component 132 (h(x)) of measurement updator 118.

Estimation system 100 may comprise methods for implementing prediction updator 116 and measurement updator 118. Such methods may be based on the properties of the modified Kronauer-Jewett model 112A (e.g. the degree and types of nonlinearities) and the properties of the measurement noise $w_k$ and/or process noise $v_k$. For clarity, measurement noise $w_k$ and/or process noise $v_k$ are not explicitly shown in the schematic illustration of FIG. 10. Observation of the modified Kronauer-Jewett model 112A highlights three features which may be used to implement methods for implementing prediction updator 116 and measurement updator 118:

the phase state φ has a nonlinear parameter space;
the state transition equation (20) is nonlinear in a way that may lead to bimodal probability densities; and
the unknown variability of light input I should be treated parametrically rather than as an additive, independent Gaussian random variable.

A typical assumption for many systems is that the state vector exists in independent linear parameter spaces of continuous real numbers such that $x \in \mathbb{R}^n$. This assumption is not the case for the state vector x of the modified Kronauer-Jewett model 112A (equation (14)). The amplitude state variable A and light response state variable n have typical parameter spaces; however, the phase offset state variable φ is an exception. By its definition, φ indicates a phase point within a twenty-four hour day, which like the hour hand of a clock is constrained to the range $0 \leq \phi < 24$ and is in a circular parameter space where the time of 0 h00 is equivalent to 24 h00. The parameter space of the phase state variable φ can be thus defined using the modulo operator as $\phi (\mathbb{R} \mod 24)$.

A second observable feature of modified Kronauer-Jewett model 112A is that the state transition equations (20) are nonlinear. The Van de Pol oscillator equations (1), (2) contain high order terms of x and $x_c$ and the light input equations (3), (5) contain exponential and multiplicative terms. While these equations may be linearized through approximations (C. Mott, M. Huzmezan, D. Mollicone, and M. van Wollen, Modifying the human circadian pacemaker using model-based predictive control, in Proceedings of the 2003 American Control Conference, June 2003, 453-458), such linearizing approximations sacrifice accuracy. One nonlinear property of the circadian system that has been qualitatively established in the prior art is that the timing of light applied around the minima of the CBT ($CBT_{min}$), or equivalently around the calibrated phase φ=4:00 h, may lead to a divergence of phase shift directions. More particularly, if light is introduced slightly before $CBT_{min}$, it will cause a delay shift, and if light is introduced slightly after $CBT_{min}$, then it will cause an advance shift. It may be inferred that this divergence behavior could lead to bi-modal probability distributions.

A third observable nonlinearity associated with the modified Kronauer-Jewett model 112A is that variability in light input I may not be accurately modeled by a simple additive Gaussian random variable in the form of I=I+v. Two factors relating to the light exposure experienced by a subject are the timing of light exposure changes relative to sleep and wake transitions and light levels which may be related to subject location (e.g. sunlight, dim room, bright room). In particular embodiments, an assumption may be made that light input may be specified as a function of a light timing parameter and light level parameter. It then follows that uncertainty should be introduced as random variability to the light timing and light level parameter values. While not wishing to be bound by any theory or method of operation, it is believed that this assumption (i.e. that light exposure should be characterized by a light timing parameter and a light level parameter) would be more representative of typical scenarios than using a simple additive noise, as light timing and light level parameters would more closely model human behavioral characteristics. According to this assumption, estimation system 100 (FIG. 10) may be provided with the general capacity to model nonlinear light input variability.

Implementing a recursive Bayesian filter for a given system requires developing solutions to prediction update equation (22) and measurement update equation (24). For linear systems with Gaussian noise, analytical solutions may exist resulting in the classical Kalman filter. However, approximation methods and approximate solutions are usually used in cases with nonlinearities. In particular embodiments, particle-filter-based methods are used to implement prediction updator 116 and measurement updator 118. In general, particle filters represent probability distributions using a number of point masses (also referred to as particles). A particle representation is an approximation wherein the approximation accuracy tends to increase with the number of particles.

Particle Filter Design

Particular embodiments of the invention involve particle filtering methods which may be referred to as Sequential Importance Resampling with a Markov chain Monte Carlo move step.

Particle filters according to particular embodiments of the invention may comprise a sequence of operations that propagate a set of particles through a recursive Bayesian filter operation of the form of Bayesian estimation method 200 (FIG. 9). Particle filters according to particular embodiments of the invention may comprise one or more additional steps (i.e. in addition to those in the general Bayesian estimation method 200) to improve stability and/or optimize performance of the particle filter. These additional steps may be performed within the functional blocks of Bayesian estimation method 200 (e.g. as a part of prediction update block 204 and/or as part of measurement update block 208) or in additional functional blocks that may be added to Bayesian estimation method 200. Such additional steps may be configured to avoid altering the probability distributions promulgated by prediction update block 204 and measurement update block 208, but may alter various mathematical properties to improve stability and/or optimize performance of the particle filter.

Figure 11:
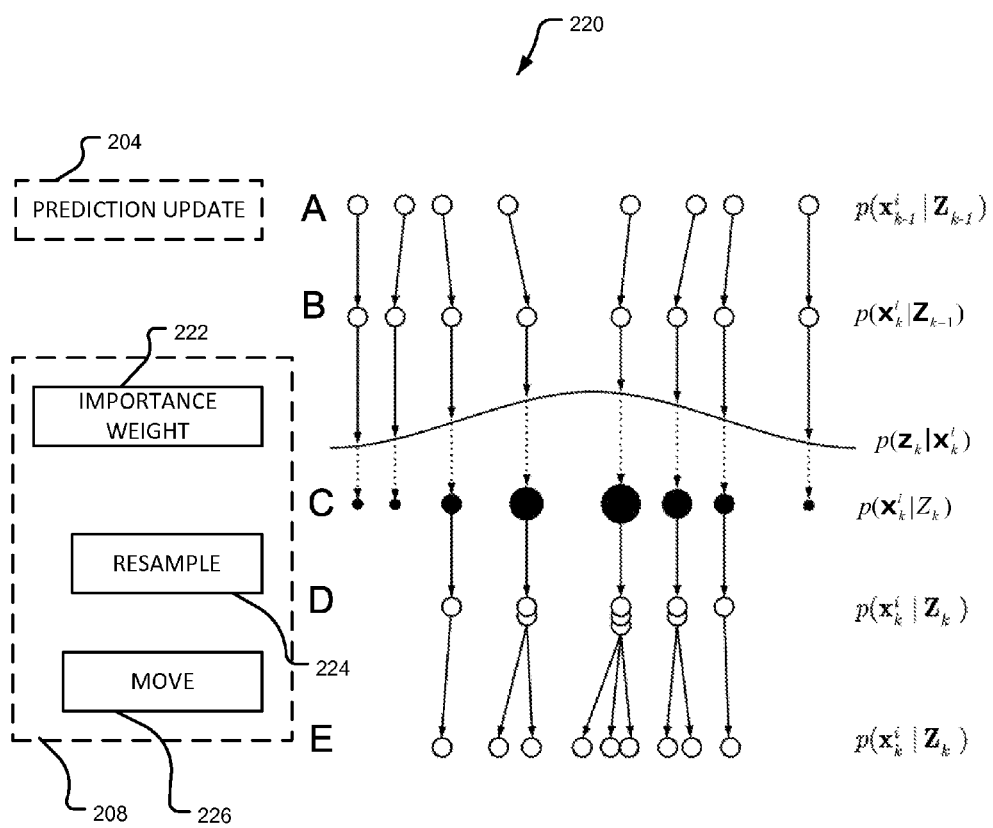
FIG. 11 schematically depicts a particle filtering method according to a particular embodiment of the invention.

FIG. 11 schematically depicts a particle filtering method 220 according to a particular embodiment of the invention. As discussed above, particle filtering method 220 follows the general procedure of Bayesian estimation method 200 (FIG. 9). The FIG. 11 illustration shows prediction update block 204 and measurement update block 208 in more particular detail and also shows a schematic illustration of a number of particles as they propagate through one iteration of method 220. The FIG. 11 illustration begins with a particle distribution A which represents the state vector's prior PDF at time step k−1 (i.e. $p(x^i_{k-1}|Z_{k-1})$). Referring to FIG. 9, the particle distribution A may arise from any of the three paths leading to prediction update block 204. In particle filtering method 220 illustrated in FIG. 11, prediction update block 204 serves to propagate the particles of particle distribution A based on the state transition model of modified Kronauer-Jewett model 112A. The output of prediction update block 204 is the particle distribution B which represents the PDF of the state vector at the time step k (i.e. $p(x^i_k|Z_{k-1})$). Referring to Bayesian estimation method 200 (FIG. 9), particle distribution B represents the output of prediction update block 204. FIG. 12A shows a pseudocode procedure for implementing prediction update block 204 of method 220 according to a particular embodiment of the invention.

Particle distribution B is then received at measurement update block 208. In the illustrated particle filtering method 220 of FIG. 11, measurement update block 208 comprises an IMPORTANCE WEIGHT block 222. IMPORTANCE WEIGHT block 222 assigns a weight to each particle in particle distribution B based on the likelihood function from the current observed data point at time $t_k$ (i.e. $p(z_k|x^i_k)$). In the illustration of FIG. 11, the likelihood function $p(z_k|x^i_k)$ is schematically depicted as a horizontally extending curve. In applying weights to particles based on likelihood function $p(z_k|x^i_k)$, IMPORTANCE WEIGHT block 222 performs the function of measurement update equation (24) and measurement update block 208 of Bayesian estimation method 200 (FIG. 9) and the output of IMPORTANCE WEIGHT block 222 is a distribution C of weighted particles which represents the posterior probability density $p(x^i_k|Z_k)$. In the schematic illustration of FIG. 11, the sizes of the colored particles in particle distribution C are representative of their weights. FIG. 12B shows a pseudocode procedure for implementing MEASUREMENT WEIGHT block 222 of method 220 according to a particular embodiment of the invention.

Particle distribution C is then provided to RESAMPLE block 224. RESAMPLE block 224 performs a thresholding process to discard particles in areas of low probability (i.e. particles with relatively low weights in distribution C). RESAMPLE block 224 also multiplies the particles in area of high probability (i.e. particles with relatively high weights in distribution C). The result of RESAMPLE block 224 is particle distribution D shown in FIG. 11. Preferably, RESAMPLE block 224 does not significantly impact the PDF of the particles—i.e. the PDF of particle distribution D is at least approximately equivalent to the PDF of particle distribution C. That is, particle distribution D still represents the posterior probability density $p(x^i_k|Z_k)$. FIG. 12C shows a pseudocode procedure for implementing RESAMPLE block 224 of method 220 according to a particular embodiment of the invention.

While particle distribution D now represents the desired posterior probability density $p(x^i_k|Z_k)$, a practical issue is that RESAMPLING block 224 reduces the diversity of the particle locations. If left in the form of particle distribution D, the particles would eventually (i.e. after a sufficient number of iterations) collapse to a single point. Accordingly, particle filtering method 220 comprises a MOVE block 226 which receives particle distribution D and redistributes the particles to output particle distribution E. Preferably, MOVE block 226 maintains (at least approximately) the statistical distribution characteristics of particle distribution D. In particular embodiments, MOVE block 226 comprises a Markov chain Monte Carlo (MCMC) procedure, which may be implemented using a Metropolis-Hastings technique. FIG. 12D shows a pseudocode procedure for implementing MOVE block 226 of method 220 according to a particular embodiment of the invention.

After MOVE block 226, the particles in distribution E are fed back to prediction update block 204 for another iteration.

Probability Density Reconstruction

While particle distributions represent probability distributions sufficiently well for use in particle filtering Bayesian estimation methods, particle distributions may be difficult to use for drawing conclusions about belief in the state variables (e.g. circadian phase φ) that they represent. Continuous PDFs may be better suited for extracting and communicating information. The invention may optionally comprise methods for reconstructing continuous PDFs from particle distributions.

In one particular embodiment of the invention, a kernel density based method is used to reconstruct continuous PDFs from particle distributions. The kernel density method involves replacing each particle with a continuous "kernel" function. Given a set of particles:

$$\sum_{i=1}^{N} \delta(x_i) \qquad (25)$$

and a kernel function w(x), an approximation of the continuous PDF is given by:

$$\hat{p}(x) = \sum_{i=1}^{N} w(x_i) \qquad (26)$$

Figures 13A, 13B, 13C:
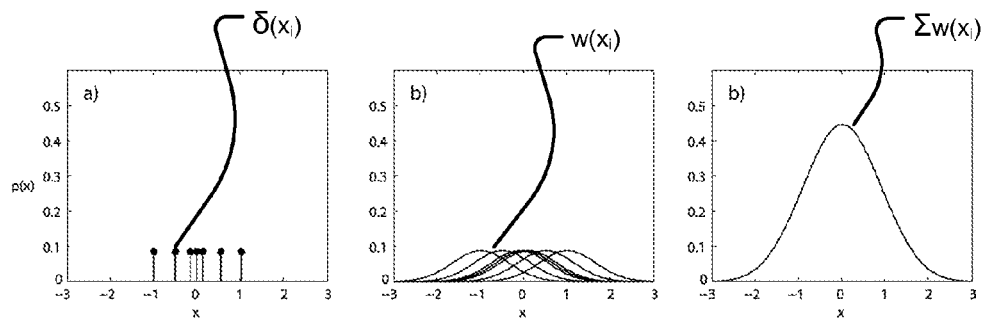
FIGS. 13A, 13B and 13C schematically depict an example of a Gaussian kernel replacement to reconstruct a continuous PDF from a particle distribution according to a particular embodiment of the invention.

The kernel function w(x) may be selected to be a Gaussian PDF (although other PDFs kernel functions may be used). An example of a Gaussian kernel replacement is shown in FIGS. 13A, 13B and 13C, where FIG. 13A shows the individual particles ($\delta(x_i)$), FIG. 13B shows the individual kernel functions ($w(x_i)$) used to replace the particles ($\delta(x_i)$) and FIG. 13C shows the superposition of the kernel functions ($w(x_i)$) according to equation (26).

Achieving accurate PDF reconstructions using kernel based techniques involves selecting two interrelated parameters: the shape of the kernel function; and the number of particles. The primary shape parameter of a kernel is its bandwidth (also referred to as its width). For Gaussian kernel functions, the standard deviation is considered the corresponding bandwidth parameter. Based on observations from known test case(s), it is known that the accuracy of a kernel based PDF reconstruction technique always increases with the number of particles. Accordingly, more particles are desirable subject to limits on computational resources. However, it may be shown that PDF reconstruction can diverge if the bandwidth is selected to be too high or too low.

To address this challenge a class of optimization solutions referred to as Kernel Density Estimators (KDEs) have been developed for selecting kernel bandwidths based on minimization of the mean integrated squared error (MISE) for a given set of particles. In particular embodiments, a KDE method based on a dual-tree algorithm (A. Gray and Moore, "Very fast multivariate kernel density estimation using via computational geometry," in Proceedings of Joint Stat. Meeting, 2003.) and selected from a Matlab KDE toolbox (A. Ihler, "Kernel density estimation toolbox for MATLAB," http://www.ics.uci.edu/ihler/code/kde.shtml, 2003) may be used here to implement KDE and to select the standard deviation of the Gaussian kernel functions. This KDE-based bandwidth selection technique is well described in the art and is not reproduced here.

Simulation Examples

The particle filter approach to circadian phase estimation (e.g. methods 200 and 220) in conjunction with the modified Kronauer-Jewett model 112A provide the capability for real-time tracking of a subject's circadian phase φ with Bayesian probability distributions. To explore the theoretical capabilities and limitations of this approach and to determine appropriate tuning parameters for the particle filter, the inventors have performed simulations for a series of scenarios with different particle filter parameter choices, light input assumptions, and noise models.

Simulation Scenario 1

A preliminary simulation scenario was designed to explore the tuning parameter selection of the number of particles and the level of process noise. A typical light input scenario was used to test the performance of the particle filter with various combinations of the tuning parameters. As a typical scenario, the light input was set to a pattern representative of an individual consistently following a standard sleep schedule for seven days. Lights were turned off at midnight for an eight hour sleep episode and then turned on at 8:00 AM. This simulation scenario also assumes a consistent light intensity of 600 Lux throughout the day.

Particle filter based Bayesian estimation method 200, 220 was tested by using a uniformly distributed initial particle distribution and observing the convergence after multiple simulation days. This test implies a case in which no a priori information is known about the individual's circadian phase φ and it is desired to estimate a PDF which indicates a degree of belief in the location of the circadian phase φ after a period of time. The time period of the simulation was selected to be one week. The expected result is that an entrainment effect will occur and the PDF representation of the phase φ will converge with a mean of φ=4.

This simulation was run seven times with different numbers of particles and, in a first case, the simulation was run without process noise. The settings for simulation scenario 1 are shown in Table 3.

TABLE 3

Simulation 1 with no process noise Parameter Values

| Parameter | Value | | | | | | |
|---|---|---|---|---|---|---|---|
| No. Particles | 12 | 24 | 48 | 72 | 240 | 480 | 960 |
| Initial distribution | Uniform over [0, 24] | | | | | | |
| Process Noise, $Q_\phi$ | (negligible) | | | | | | |
| Light levels | | | | | | | |
| Dark | 0 Lux | | | | | | |
| Bright | 600 Lux | | | | | | |
| Measurements | (none) | | | | | | |

A second set of simulations was run, repeating the choice of particle numbers from the first case, but this time with the phase state process noise set to a non-negligible value of $Q=3\times10^{-4}$. Since there was no quantitative data from which a process noise level can be selected, this value was chosen based on qualitative physical assumptions about variability inherent in the circadian pacemaker system. The settings for the second set of simulations are shown in Table 4.

TABLE 4

Simulation 1 with process noise Parameter Values

| Parameter | Value | | | | | | |
|---|---|---|---|---|---|---|---|
| No. Particles | 12 | 24 | 48 | 72 | 240 | 480 | 960 |
| Initial distribution | Uniform over [0, 24] | | | | | | |
| Process Noise, $Q_\phi$ | $3 \times 10^{-4}$ | | | | | | |
| Light levels | | | | | | | |
| Dark | 0 Lux | | | | | | |
| Bright | 600 Lux | | | | | | |
| Measurements | (none) | | | | | | |

Figure 14:
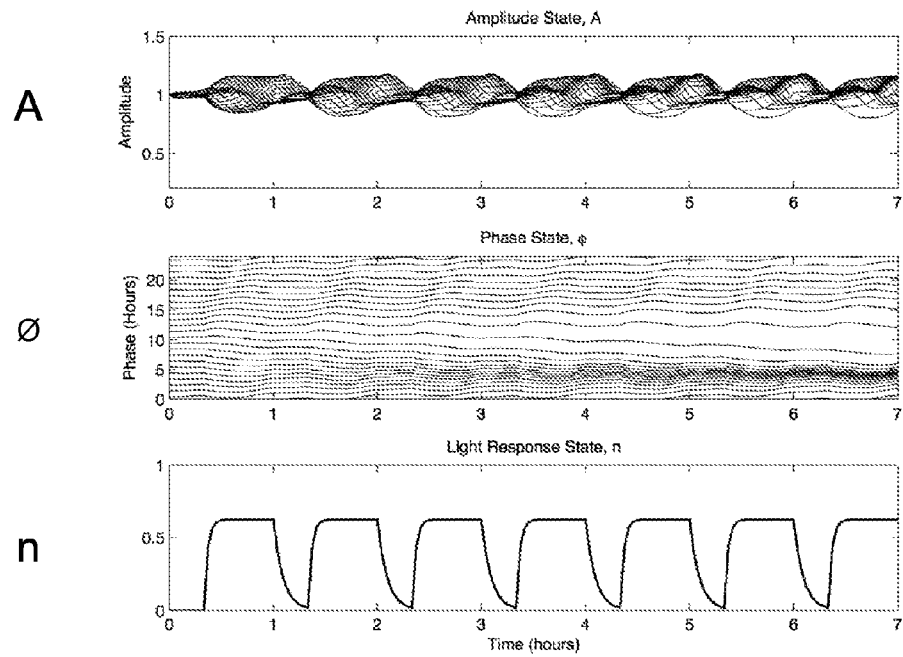
FIG. 14 shows a number of plots of simulated data relating to state variables in a first simulation scenario with a 24 point particle filter.

These two sets of simulations yield results from 14 different trials. FIG. 14 illustrates the state variables A, φ, n for a single simulation with 24 particles and no process noise. With only twenty-four particles and negligible process noise, the second plot of FIG. 14 illustrates the precise path of each phase particle during the simulation. It may be observed from the second FIG. 14 plot, that the phase of the particles becomes further entrained to the timing of the sleep/wake schedule after each light exposure period and have a mean of approximately 4:00 AM as expected.

The scenario 1 simulation results were used to select a number of particles by examining the phase PDF of each simulation after the seven day period. The selection of an appropriate number of particles may be based on the number of particles above which increasing numbers of particles still converges to substantially the same distribution. Based on the scenario 1 simulations with process noise, it was observed that the phase PDFs using 240, 480 and 960 particles were substantially similar to one another. Accordingly, for a process noise of $Q=3\times10^{-4}$, it is desirable to select a number of particles N>=240 to achieve convergence to an accurate phase PDF. In the other simulations described herein, a default value of N=240 will was used to minimize computational complexity. The optimal number of particles may vary for different simulation scenarios (e.g. different levels of process noise). Choosing a high number of particles may improve accuracy of the results with no penalty except for computational resources.

Simulation Scenario 2

This simulation scenario further examines the predictions of entrainment to a fixed schedule and tests different noise models. This scenario simulated the case of an individual following a consistently timed eight hour sleep regimen (between 12:00 AM and 8:00 AM) for a duration of three weeks. The waking light levels were chosen to be typical of indoor bright light of 380 Lux. In a case in which no a priori information is known about the individual's circadian phase φ, the final phase PDF indicates a degree of belief in the location of the circadian phase φ after the three weeks on this schedule. This analysis has a significant connection to a clinical scenario since a three-week monitoring period is typically used to ensure that subjects have a well entrained circadian phase prior to entering a laboratory study. The distribution of the final phase PDF will give an indication as to the strength of that assumption.

To illustrate the effects of noise parameters, three different simulations were conducted using the same baseline schedule. In the first case, no noise sources were included, in the second case, process noise was added to the phase state and in the third case, a further random variability was introduced to the light input. The light variability was introduced as a first Gaussian random variation in the timing of each light to dark transition with variance $Q_t$, and a second Gaussian random variation in the light level with variance $Q_L$. The parameters for each of the three simulations are set out in Table 5.

TABLE 5

Simulation 2 Parameter Values

| Parameter | Value Case 2A | | |
|---|---|---|---|
| No. Particles | 240 | 240 | 240 |
| Initial distribution | Uniform over [0, 24] | | |
| Process Noise, $Q_\phi$ | $1 \times 10^{-9}$ | $3 \times 10^{-4}$ | $3 \times 10^{-4}$ |
| Light levels | | | |
| Dark | 0 Lux | | |
| Bright | 380 Lux | | |
| Light Noise | | | |
| $Q_t$ | 0 | 0 | 2 |
| $Q_L$ | 0 | 0 | 50 |
| Measurements | (none) | | |

Figure 15:
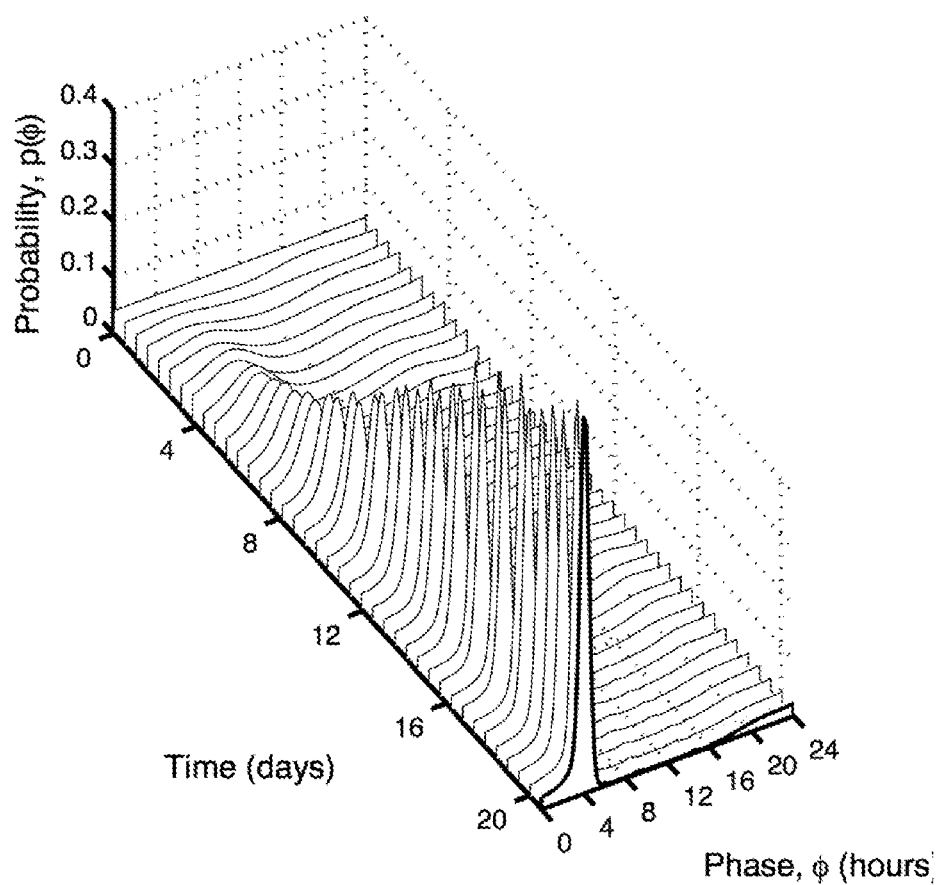
FIG. 15 shows phase PDFs generated by a second simulation scenario with no noise.

FIG. 15 shows the phase PDF predicted over the course of the 21 day period for the simulation with no noise. At day 21, the maximum likelihood of the phase φ occurs around 4:00 AM, which corresponds to the expected result for an individual synchronized to a regular sleep-wake cycle. When process noise is introduced in the second simulation of scenario 2, there is a broadening of the probability distribution which can be seen in FIG. 16. FIG. 17 shows the phase PDF for the third simulation of scenario 2, with additional variability in the light input. This third case shows a further widening of the phase PDF which represents additional uncertainty in the location of the circadian phase φ.

Figure 16:
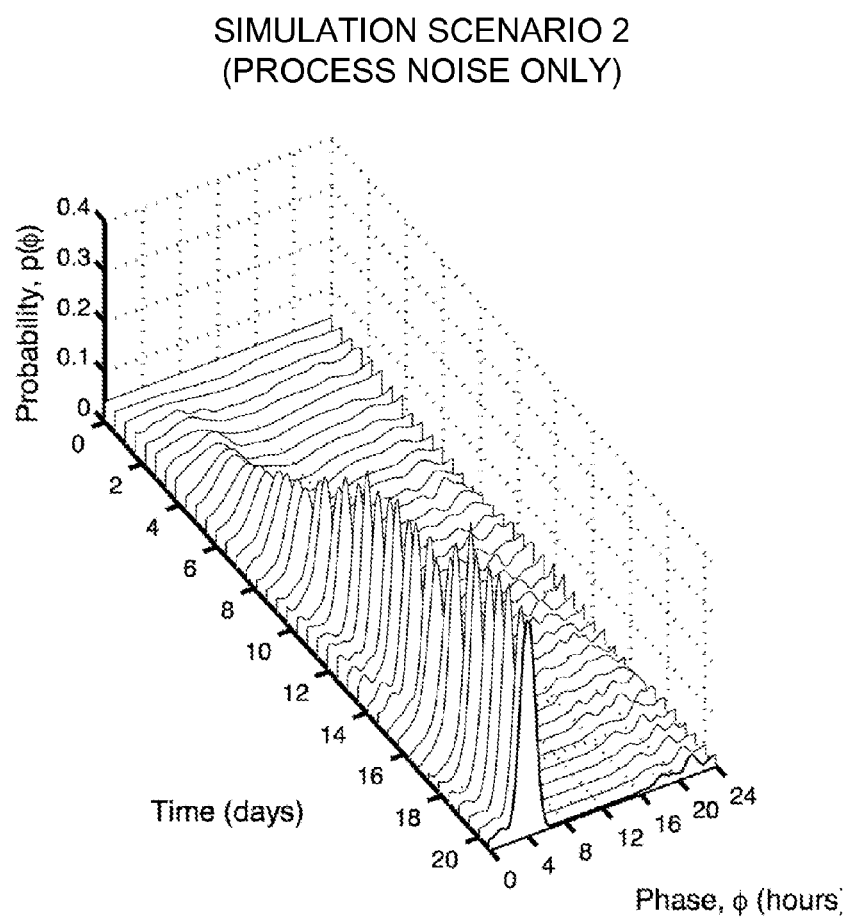
FIG. 16 shows phase PDFs generated by the second simulation scenario with process noise.
Figure 17:
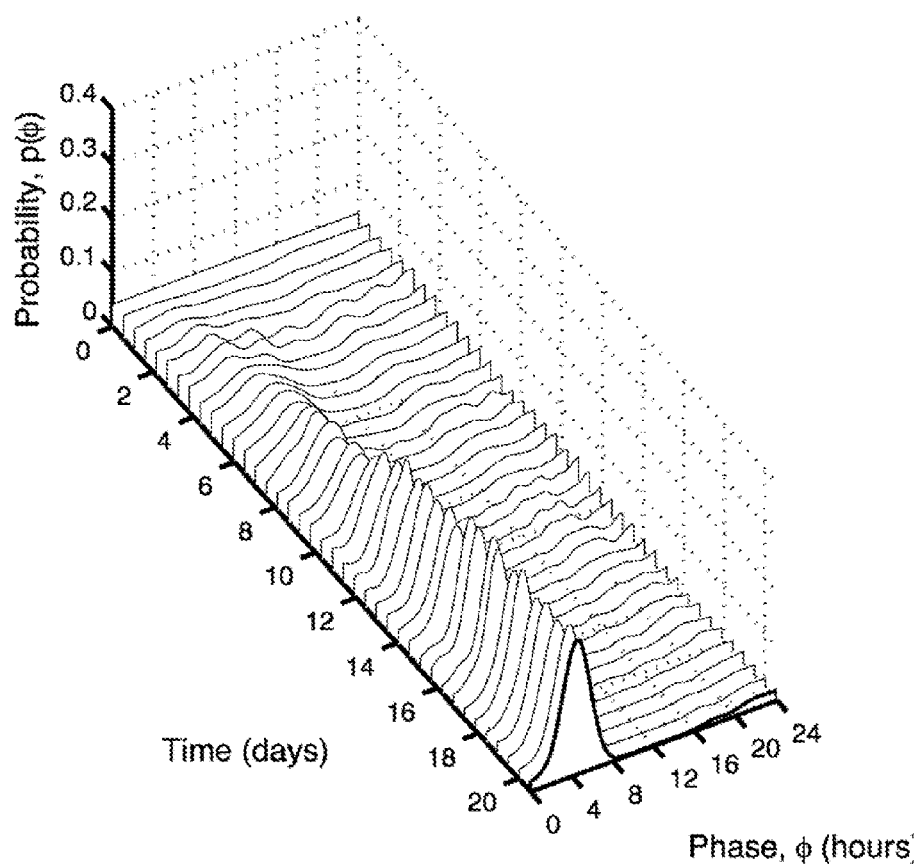
FIG. 17 shows phase PDFs generated by the second simulation scenario with process noise and light input noise.

Another interesting observation can be made by comparing FIGS. 15, 16 and 17. With the introduction of process noise (i.e. FIG. 16), the peak probability was reduced, but the mean was substantially unchanged. However, the introduction of light variability (FIG. 17) had the interesting effect of skewing the mean of the phase PDF forward.

Simulation Scenario 3

Figure 18:
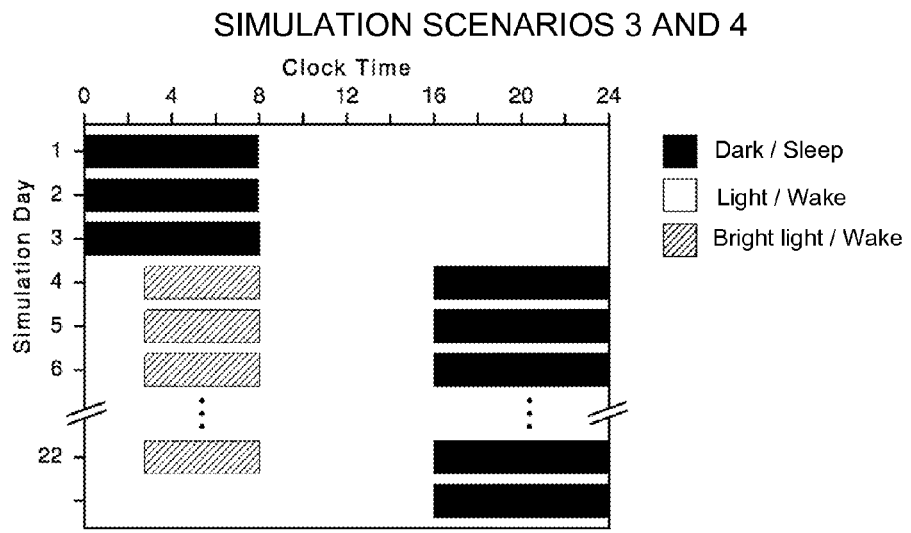
FIG. 18 schematically depicts the light pattern used for third and fourth simulation scenarios.

A third simulation scenario was conducted to explore phase shifting properties of the circadian pacemaker model in response to a scenario where an individual makes an abrupt eight hour advance in their sleep/wake schedule, as can happen with transmeridian airplane travel for example. As shown experimentally (D. Boivin and F. James, Phase-dependent effect of room light exposure in a 5-h advance of the sleep-wake cycle: Implications for jet lag, Journal of Biological Rhythms, vol. 17:3, 266-267, June 2002.), and predicted by the Kronauer-Jewett model, the introduction of strong light pulses at appropriate circadian phases will increase the rate of adjustment to a shifted schedule. The greatest effect is achieved by introducing light near the nadir of the circadian phase (i.e. around φ=4:00 h) when the light response is most sensitive, however the phase nadir is also the critical point at which phase shifts may occur in opposite directions on either side of the phase nadir. Therefore, by introducing light near the phase nadir there is a risk of causing a shift in the opposite direction to the one desired. With the Bayesian estimation particle filter methods 200, 220 we can test the probabilistic outcomes of phase shift direction. The light and sleep/wake patterns for the scenario 3 simulations are shown in FIG. 18. A bright light pulse was chosen with a duration of five hours, starting at time 3:00 as shown in FIG. 18. The simulation parameters for the scenario 3 simulation (shown in Table 6)

are identical to those of the second case of simulation scenario 2, except that the initial condition is set to a known prior distribution that represents an individual well entrained to the initial schedule.

TABLE 6

Simulation 3 Parameter Values

| Parameter | Value |
|---|---|
| No. Particles | 240 |
| Initial distribution | Gaussian N(4.38, 1.3) |
| Process Noise, $Q_\phi$ | $3 \times 10^{-4}$ |
| Light levels | |
| Dark | 0 Lux |
| Typical | 380 Lux |
| Bright | 10000 Lux |
| Measurements | (none) |

Figure 19:
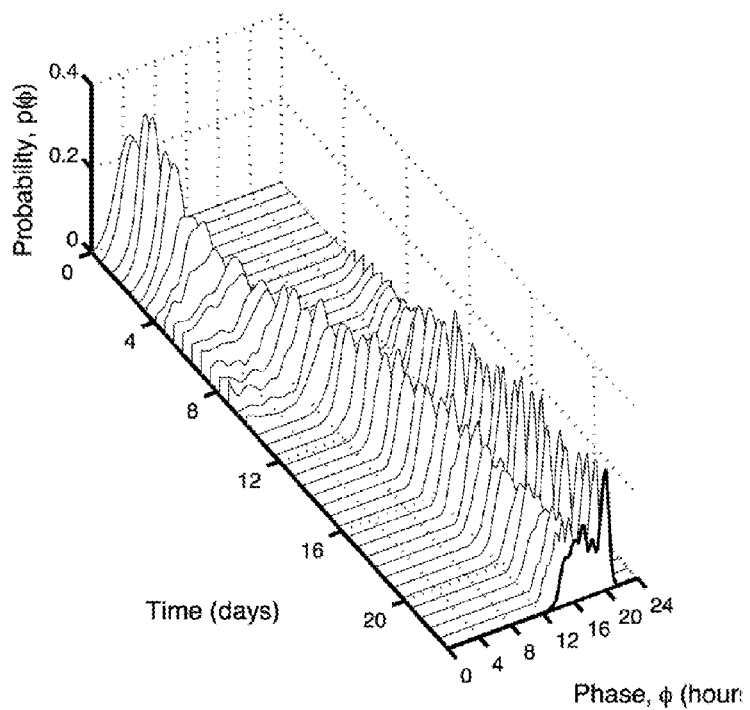
FIG. 19 shows phase PDFs generated by a third simulation scenario.

FIG. 19 shows the phase PDFs for simulation scenario 3. It may be observed from FIG. 19 that there is a split in the probability distribution after the first introduction of the light pulse. The optimal adjustment to the new schedule occurs on the phase trajectory which decreases to zero and then "wraps around" the 0 h/24 h boundary to stabilize at 22 h by day twelve (ten days after the shift). The other phase trajectory, in which the phase increases from 4 h toward 22 h doesn't entrain to the new schedule until about day 23 (twenty-one days after the shift), which is twice as long. While the divergent shift behavior has been captured in the prior art Kronauer-Jewett model 112, the capability to analyze probabilistic scenarios in this manner has not been possible previously.

Simulation Scenario 4

Simulation scenario 4 incorporates physiological measurement feedback. The sleep/wake and light pattern used in simulation scenario 4 were the same as those applied in simulation scenario 3 (FIG. 18) where the simulation predicted a bimodal phase PDF resulting from the introduction of bright light stimulus around the circadian phase nadir (i.e. around $\phi=4:00$ h). It will be appreciated that the bimodal phase PDF of simulation scenario 3 could lead to difficulty making phase prediction decisions, because the two phase PDF trajectories lead to two possible scenarios which are diametrically opposed in their physiological circadian effects. It was expected that incorporating physiological measurements into the simulation in simulation scenario 4 would enhance the phase prediction ability of the system, as a small set of measurements could resolve the ambiguity between two possible trajectories. Simulation scenario 4 involved selecting the phase trajectory in which phase of the individual advances (i.e. on the lower "wrap-around" trajectory of FIG. 19). This selection was accomplished by adding two phase measurements at day 6 and day 8 and using the assumption that the phase measurements have accurate means but relatively low measurement precision $\sigma^2=3$. The parameters of simulation scenario 4 are shown in Table 7.

TABLE 7

Simulation 4 Parameter Values

| Parameter | Value |
|---|---|
| No. Particles | 240 |
| Initial distribution | Gaussian N(4.38, 1.3) |
| Process Noise, $Q_\phi$ | $3 \times 10^{-4}$ |

TABLE 7-continued

Simulation 4 Parameter Values

| Parameter | Value |
|---|---|
| Light levels | |
| Dark | 0 Lux |
| Typical | 380 Lux |
| Bright | 10000 Lux |
| Measurements | $\theta(6\,d) = 1 \pm 3$ |
| | $\theta(8\,d) = 22 \pm 3$ |

Figure 20:
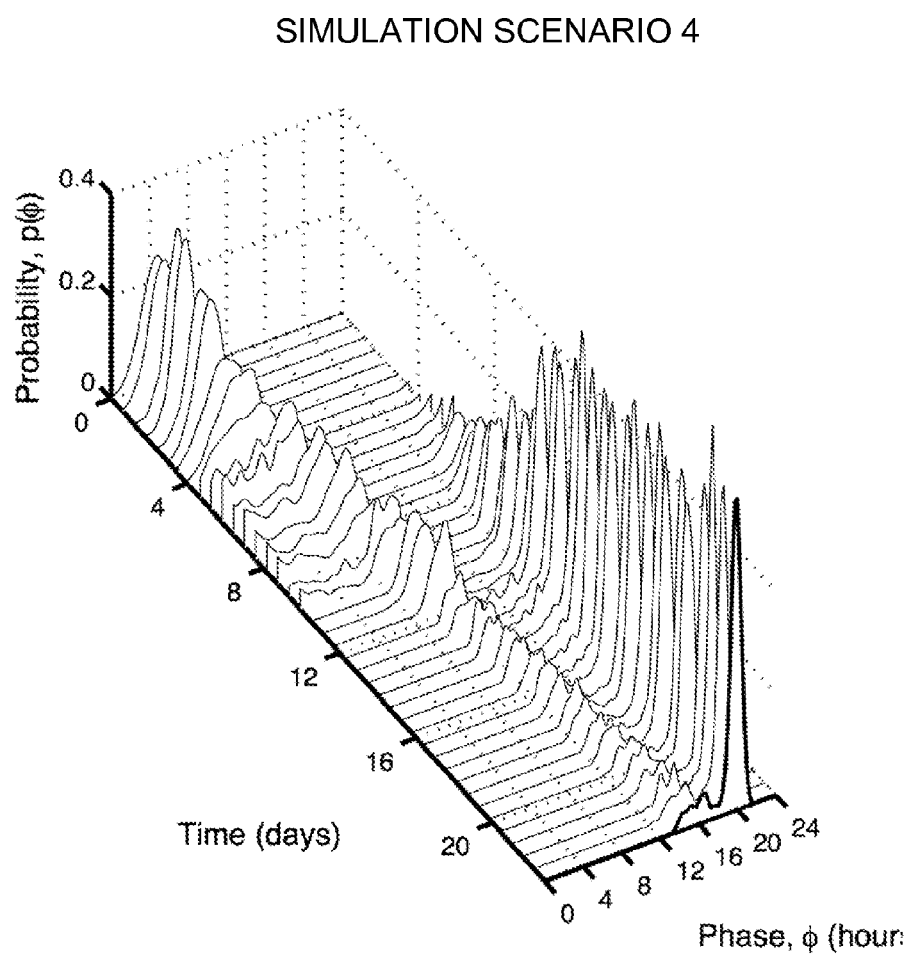
FIG. 20 shows phase PDFs generated by a fourth simulation scenario.

The phase PDF results of simulation scenario 4 are shown in FIG. 20. Comparing the phase PDF trajectories of FIG. 20 (simulation scenario 4) to those of FIG. 19 (simulation scenario 3), it is apparent that the measurement information incorporated into scenario 4 has provided sufficient information to determine that the individual has a high probability of being on the lower ("wrap around") trajectory. Considering real world applications in ambulatory, non-laboratory settings, sensors will not have the same degree of precision as in controlled, laboratory environments. For such applications, the capability to integrate multiple somewhat noisy measurements in the manner of simulation scenario 4 will be advantageous.

Human Subject Example

The modified Kronauer-Jewett model 112A of the Bayesian particle filtering methods 200, 220 does not have any customized tuning parameters so it remains a fixed component. However, different types of optional physiological inputs 104 may be provided to the estimation system 100. As discussed above, physiological inputs 104 typically require physiological sensors (e.g. sensors 120 of FIG. 8). Such sensors may be invasive or non-invasive and may be ambulatory (i.e. allowing the subject freedom of movement) or non-ambulatory (restricting subject movement). Examples of invasively measurable physiological parameters include, without limitation, CBT (which may be measured rectally), salivary melatonin assays and salivary cortisol assays. Examples of non-invasively measurable physiological parameters include, without limitation, body temperature (which may be measured by a cerebral temperature sensor), physical activity (which may be measured by an actigraph (e.g. a wrist-mounted actigraph), for example) and heart rate (which may be measured by ECG in a Lifeshirt™, for example).

As discussed above, circadian phase markers for the temperatures and hormone levels may be determined (e.g. in phase estimators 124 of FIG. 8) with direct application of a Fourier fit combined with feature detection (e.g. maxima or minima detection) location and suitable marker-to-phase conversion (e.g. time shift). As discussed above, measured temperature markers may be determined with a second-order or third-order Fourier fit using a minimum point feature and may be appropriately converted (e.g. by 0.8 h time shift) to correlate to circadian phase $\phi$. With melatonin and cortisol, a second and/or third order Fourier fit using a maximum point feature may be selected. However, there are a variety of different phase analysis options which may be selected to convert melatonin and cortisol markers to correlate to circadian phase $\phi$ (E. Klerman, H. Gershengorn, J. Duffy, and R. Kronauer, Comparisons of the variability of three markers of the human circadian pacemaker, Journal of Biological Rhythms, 17: 2, 181-193, 2002). It has been shown that the melatonin maxima occurs approximately 2.3 hours before CBT minima. Consequently, conversion of melatonin markers (maxima) to circadian phase φ may involve a time shift of $\tau_{MEL}$=2.3 h–0.8 h=1.5 h. The cortisol maxima occurs approximately 2.2 hours after CBT minima and may therefore be converted to circadian phase φ by a time shift of $\tau_{CORT}$=–2.2 h–0.8 h=–3.0 h.

Figure 21:
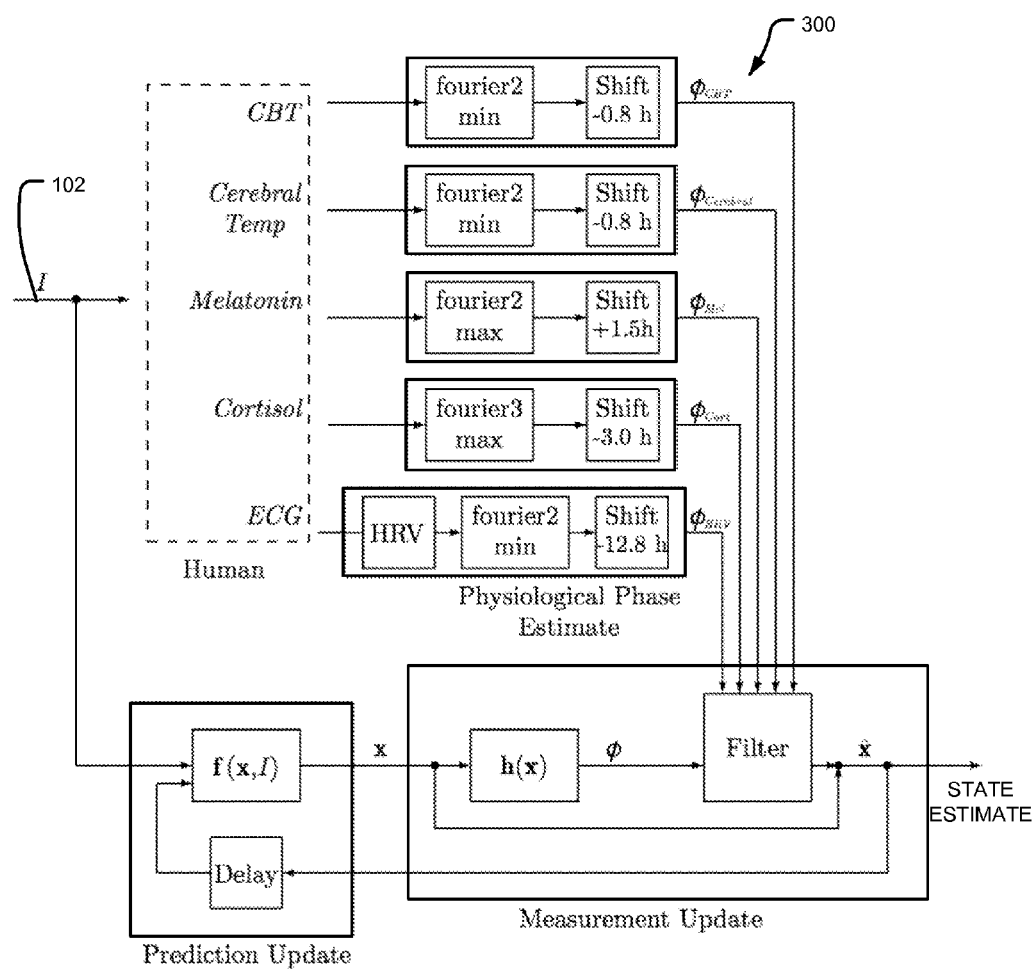
FIG. 21 is schematic illustration of an experimental phase prediction system according to a particular embodiment.

These physiological measurements were incorporated into an experimental phase prediction system 300. A schematic illustration of this experimental phase prediction system 300 is shown in FIG. 21. A motivating objective involves determination of phase estimates based on non-invasive and ambulatory measurements, so a comparison was made between the invasive and noninvasive physiological measurements. In this experiment, the available information for the subject which can be applied to the phase estimation system includes the sleep history prior to the subject entering the lab, the known light exposure during the experiment and noninvasive physiological data collected when the subject is ambulatory.

Figure 22A:
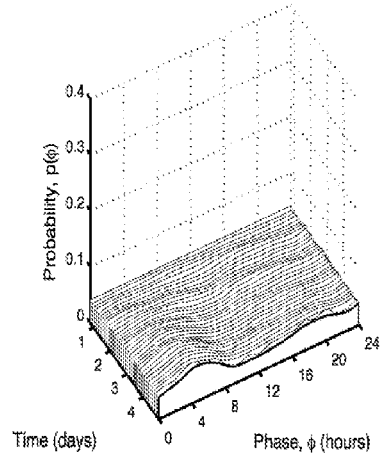
FIG. 22A shows phase PDFs generated by the FIG. 21 system for a human subject without incorporation of prior sleep history information.
Figure 23A:
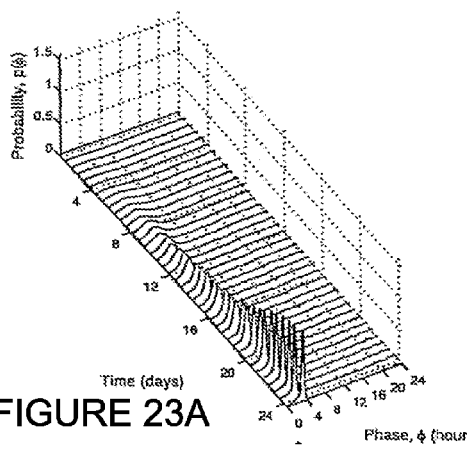
FIGS. 23A, 23B and 23C respectively show the evolution of the phase PDFs of a human subject experiment in the cases of a Bayesian particle filter estimation without physiological measurement information (FIG. 23A), a CBT measurement only (FIG. 23B) and a Bayesian particle filter estimation with CBT measurement information (23C)
Figure 23C:
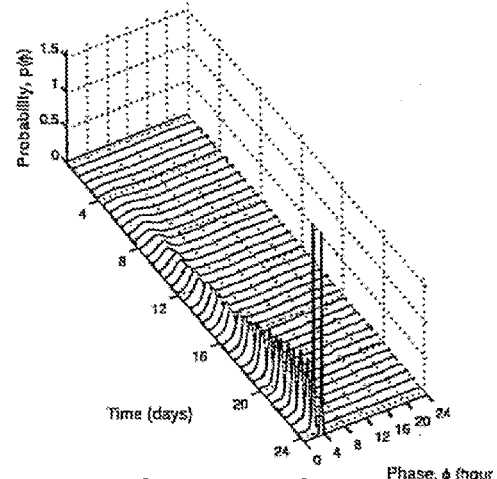

A first data set was generated based only on the light exposure during the experiment—i.e. where the subject's circadian phase prior to the experiment was considered completely unknown. The resulting phase PDFs are shown in FIG. 22A. A second data set was generated by adding knowledge of the subject's sleep history which was kept in a log prior to the experiment. A number of assumptions are made in this sleep history analysis since the exact light levels were not known and uncertainty surrounding the accuracy of the sleep log was unknown. Light was assumed to be constant at 380 Lux for the duration of waking. The resulting phase PDFs for the second data set are shown in FIG. 23A. As can be seen by comparing FIGS. 22A and 23A, the second data set which incorporates sleep history, results in narrower phase PDFs, reflecting the additional information.

Figure 23B:
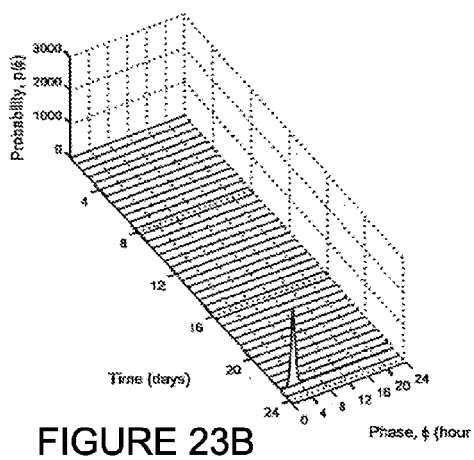

After 59 hours, a constant routine scenario was used in a laboratory setting. Monitoring from all ambulatory sensors was maintained through the constant routine with the addition of the cerebral temperature sensor, melatonin assay and cortisol assay. After the deriving the phase markers of the various physiological inputs, the PDFs of the phase markers were converted to the calibrated phase domain. It was observed that the temperature and melatonin markers predict relatively consistent phase information, but that the cortisol phase prediction was slightly different than that predicted by the other physiological markers. The PDF of the core body temperature phase marker is calculated at the end of the constant routine and corresponds to estimate of circadian phase at a particular point in time as shown in FIG. 23B.

Figure 24:
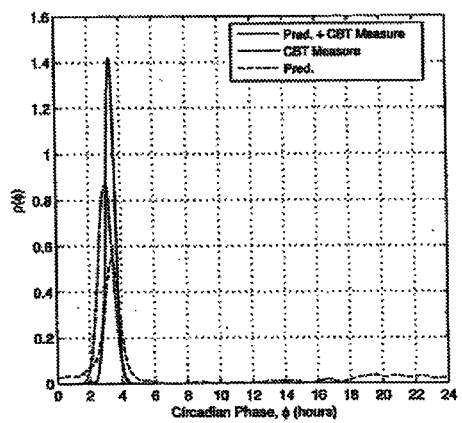
FIG. 24 shows the FIG. 23 phase PDFs at the conclusion of the human subject experiment.

FIG. 24 shows the phase PDFs generated using CBT measurement alone (without Bayesian particle filter estimation), the final phase PDF (i.e. at the conclusion of the experiment) generated using model predictions alone (without CBT phase measurement), and the final phase PDF generated using the combination of model predictions and the CBT phase estimate. The combined estimate provides a narrower PDF than either the prediction or measurement alone.

In one particular embodiment, a circadian phase estimation method/system of the type described herein (or portions thereof) may be embodied in a device mounted to a body of the subject (e.g. a wrist-mounted device). For examples, such a body-mounted device could comprise one or more of: a light sensor for providing light stimulus input 102, I, an actigraph sensor which may contribute to light stimulus input 102, I and which may comprises a physiological sensor for providing physiological input 104 (e.g. habitual sleep and/or rise times), a processor for performing the circadian phase estimation as described above and a display on which the circadian phase estimate can be displayed. Such a body-mounted device may also have suitable I/O hardware and software for communication with an external computer or external processing device.

In another particular embodiment, a circadian phase estimation system of the type described herein (or portions thereof) may be connected to or may otherwise comprise a light stimulus device, such as a light box. The circadian phase estimate may then be used to control the light stimulus device to achieve a desired circadian phase shift in the subject. In one particular embodiment, the light stimulus device may be configured to use the circadian state estimate to recommend or initiate appropriate light intervention timing and intensity for the subject to achieve a desired phase shift. In other embodiments, recommending or initiating appropriate light intervention timing and intensity may be performed by the same processor used to perform the circadian phase estimation which may in turn control the output of the light stimulus device.

Applications

The methods and systems described herein find useful applications in a variety of settings. Two general areas include monitoring circadian physiology for alertness and safety in workplace settings and monitoring circadian physiology to assist chronotherapeutic treatments. Circadian rhythms significantly affect human health and safety, and there are a number of applications where knowledge of an individual's circadian phase would prove useful in mitigating risks or delivering therapeutic treatment.

Alertness and Safety

Individuals required to perform critical tasks when their circadian pacemaker is coordinating the body's metabolic and endocrine systems for sleep experience significant impairments in performance which increases the risk of accidents. Many industrial workplace scenarios involve tasks demanding a high degree of alertness and reliability in addition to requiring workers to operate on irregular or shifting schedules. As a result of schedule variations, individuals experience reduced levels of alertness and cognitive performance due to both sleep loss and circadian rhythm desynchrony. The associated risk of accidents is a concern in operational settings, such as, by way of non-limiting example, transportation, health care delivery and emergency response. Accidents at the Chernobyl and Three Mile Island nuclear power plants, the NASA Challenger disaster, and the Exxon oil spill in Valdez, Ak. may all be partially attributable to decrements in performance due to the effects of circadian phase and length of time awake.

Strategies to mitigate the adverse effects of circadian phase desynchrony and sleep loss in shift work environments include education programs, the design of shift work rotation schedules, and the use of light exposure to shift the endogenous circadian pacemaker. Strategies to reduce the effects of jet lag travel also include the specific timing of light exposure to accelerate adaptation to a new time zone. Implementing reliable means to shift an individual's circadian pacemaker however requires accurate knowledge of the individual's circadian phase, which is not currently possible outside of the laboratory.

In some embodiments, circadian phase estimation systems and methods of the type described herein may be used as part of systems and methods for fatigue countermeasure advisory. The estimated circadian phase may be provided to a fatigue countermeasure advisory system which may use the estimated circadian phase to improve its future predictions of fatigue and timing of countermeasures (e.g. caffeine timing) based on the circadian phase estimate.

Medical Treatment

The traditional medical concept of "homeostasis", that the human body maintains a constant internal state, is giving way to the recognition of continuous time-varying fluctuations. Applying this information, medical treatments are being developed to deliver treatment at not only the right location but at the right time. For instance, the cycles present in human circadian physiological systems bring about predictable changes in the body's tolerance to anticancer agents and a tumor's responsiveness to them. Indeed, it has been shown that the tolerability and the efficacy of chemotherapeutic drugs can vary by 50% or more as a function of dosing time in mice or rats. Circadian-modulation of continuous drug delivery systems for chemotherapy patients has been demonstrated in randomized, multi-centre trials to have enhanced tumor response and increased survival rates.

In some embodiments, circadian phase estimation systems and methods of the type described herein may be used as part of drug delivery methods and/or drug delivery systems. In particular embodiments of such drug delivery methods and/or drug delivery systems, the estimated circadian phase could be used to modulate a drug flow rate, such that the drug flow rate depends on the circadian phase. In particular embodiments, the estimated circadian phase could be used to continuously modulate the drug flow rate. In other embodiments, the circadian phase may be monitored and then a dose may be administered during a window of optimal circadian phase.

When administering chronomodulated therapy, it is desirable to synchronize treatment timing to the endogenous circadian phase of the individual being treated. In recent trials physical activity patterns measured with wrist worn accelerometers have been used to infer sleep/wake schedules and thus circadian phase. While the activity measures can lead to a general estimate of circadian phase if an individual has maintained a consistent schedule, there are known variabilities between individuals and considerable uncertainty in the method. Enhanced methods of accurately monitoring circadian phase translate to increased efficacy of chronotherapies.

Certain implementations of the invention comprise computer processors which execute software instructions which cause the processors to perform methods of the invention. For example, one or more processors in a phase estimation system may implement data processing steps in the methods described herein by executing software instructions retrieved from a program memory accessible to the processors. The invention may also be provided in the form of a program product. The program product may comprise any medium which carries a set of computer-readable instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs and DVDs, electronic data storage media including ROMs, flash RAM, or the like. The instructions may be present on the program product in encrypted and/or compressed formats.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

- One or more measured circadian phase estimate inputs $\phi$ may be received from external systems, rather than being calculated from a physiological input 104.
- Phase estimate outputs of the circadian state estimation system may be made in real-time, may be predicted into the future, or may be calculated for historical periods.
- Light input 102, I may be measured directly from light sensor, or may be estimated based on other known or assumed environmental conditions. As a non-limiting example light input could be estimated from actigraphy sensors from which sleep (dark) and wake (bright) periods are inferred.
- In the embodiments described above, circadian state estimation methods/systems make use of state-space models which model the effect of light stimulus on the circadian state of a subject. This is not necessary. Circadian-state estimation methods/systems according to particular embodiments of the invention may use other types of mathematical models which model the effect of light stimulus on the circadian phase of a subject. Such mathematical models may incorporate model variables which may be represented in the form of probability distributions that model the uncertainty in the model variables. Bayesian estimation techniques similar to those described above may be used with such mathematical models. Depending on the mathematical nature and/or complexity of such models, particle filtering techniques or other suitable approximation techniques may be used to obtain approximate solutions to Bayesian estimation problems using such mathematical models. An example of another type of mathematical model is a circadian Phase Response Curve. A Phase Response Curve model may comprise a set of response curves corresponding to various light exposure levels, where each response curve is a mathematical relationship relating a model variable of the circadian phase at time t=x, to the resulting circadian at time t=x+k when exposed to a given light intensity.
- Multiple methods for implementing Bayesian equations in the prediction updator 116 and the measurement updator 118 may be used, and may include alternate particle filter operations, or other non-particle-filter methods.
- Sensors 120, physiological phase estimators 114, and the prediction updator 116 and measurement updator 118 may be physically separate. As a non-limiting example, remote sensors may be distributed on individuals and sensor information transmitted to a physiological phase estimators, and prediction and measurement updators on a computational system.

What is claimed is:

1. A system for predicting a circadian state of an individual, the system comprising:
at least one physiological sensor connected to a processor, wherein the physiological sensor is configured to measure one or more physiological parameters from an individual related to circadian phase, and wherein the processor is configured to perform the steps of:
providing a biomathematical model comprising:
one or more model variables comprising at least a circadian phase offset model variable representative of a phase offset of the circadian state of the individual,
at least one light stimulus model input representative of light stimulus to which the individual is exposed over time, and
at least one physiological parameter model input representative of one or more physiological parameters of the individual related to circadian phase;

wherein the biomathematical model predicts the change of the circadian phase offset model variable over time based at least in part on light exposure to which the individual is exposed over time using the at least one light stimulus model input, and updates the one or more model variables based on the physiological parameter model input;

receiving an estimate of the circadian phase offset of the individual corresponding to an initial time;

receiving a physiological measurement from the physiological sensors, the physiological measurement comprising: a physiological parameter of the individual related to circadian phase, and a physiological measurement time comprising a time at which the physiological parameter is measured;

receiving one or more light stimulus measurements corresponding to light exposure to which the individual is exposed, the light stimulus measurements occurring between the initial time and the physiological measurement time, and wherein each light stimulus measurement comprises: a light stimulus intensity value, and light measurement time comprising a time at which the light stimulus intensity value is measured;

predicting a value of the circadian phase offset model variable corresponding to the physiological measurement time by applying the biomathematical model to at least the received estimate of the circadian phase offset corresponding to the initial time and the received one or more light stimulus measurements; and updating the predicted value of the circadian phase offset model variable corresponding to the physiological measurement time by applying the biomathematical model to at least the predicted value of the circadian offset model variable corresponding to the physiological measurement time and the received physiological measurement.

2. A system according to claim 1 wherein the received estimate of the circadian phase offset comprises a probability distribution function (PDF) of a phase offset of the circadian state of the individual, and wherein the circadian phase offset model variable represents a PDF of the phase offset of the circadian state of the individual.

3. A system according to claim 2 further comprising a prediction updator configured to estimate one or more PDFs of the one or more model variables at a first time step based on the received light stimulus measurements and one or more known PDFs of the one or more model variables at a second time step, the first time step subsequent to the second time step, and wherein the prediction updator is used by the processor to iterate toward the updated PDF of predicted value of the phase offset model variable.

4. A system according to claim 3 comprising a measurement updator connected to receive the at least one physiological measurement from physiological sensors and to receive the one or more PDFs of the one or more model variables at the first time step from the prediction updator, the measurement updator configured to use the at least one physiological measurement and the one or more PDFs of the one or more model variables at the first time step to estimate one or more measurement-updated PDFs of the one or more model variables at the first time step, wherein the one or more measurement-updated PDFs of the one or more model variables at the first time step take into account the at least one physiological measurement and wherein the measurement updator is used by the processor to iterate toward the updated PDF of predicted value of the phase offset model variable.

5. A system according to claim 3 comprising: a physiological phase estimator connected to receive the at least one physiological measurement from the physiological sensors, to provide one or more corresponding physiological input signals to the processor, and to estimate one or more corresponding physiological feature PDFs of the circadian phase offset model variable based on the one or more physiological input signals, each physiological feature PDF expressing a degree of confidence in a circadian phase offset model variable prediction based on the corresponding physiological input signal.

6. A system according to claim 5 comprising a measurement updator connected to receive the one or more physiological feature PDFs of the circadian phase offset from the physiological phase estimator and to receive the one or more PDFs of the one or more model variables at the first time step from the prediction updator, the measurement updator configured to use the one or more physiological feature PDFs and the one or more PDFs of the one or more model variables at the first time step to estimate one or more measurement-updated PDFs of the one or more model variables at the first time step, wherein the one or more measurement-updated PDFs of the one or more model variables at the first time step take into account the one or more physiological feature PDFs of the circadian phase offset and wherein the measurement updator is used by the processor to iterate toward the updated PDF of predicted value of the phase offset model variable.

7. A system according to claim 5 wherein the physiological phase estimator comprises, for each physiological input signal, a marker component for:

extracting a marker from the physiological input signal, the marker comprising at least one of: a feature of the physiological input signal; and a time of occurrence of the feature of the physiological input signal; and determining a marker PDF representing an uncertainty present in extracting the marker from the physiological input signal.

8. A system according to claim 7 wherein the physiological phase estimator comprises, for each physiological input signal, a marker-to-phase converter component for transforming the marker PDF into a domain of the phase offset of the individual to thereby obtain the physiological feature PDF of the phase offset.

9. A system according to claim 8 wherein the marker PDF reflects a degree of confidence in the time of occurrence of the feature within the physiological input signal and wherein the marker-to-phase converter component is configured to shift the marker PDF in the time domain to obtain the physiological feature PDF.

10. A system according to claim 7 wherein, for each physiological input signal, the marker component is configured to extract the marker from the physiological input signal by: fitting a curve to the physiological input signal; and identifying the feature in the curve, the feature comprising at least one of: a minimum of the curve; a maximum of the curve; a point where the curve crosses a threshold; and a region where the curve is located on one side of a threshold.

11. A system according to claim 10 wherein for each physiological input signal, the marker PDF reflects a degree of certainty in one or more of: the fitted curve; and the identified feature.

12. A system according to claim 1 wherein the processor is further configured to repeat one or more times the steps of:

receiving an estimate of the circadian phase offset of the individual corresponding to an initial time;

receiving a physiological measurement from the physiological sensors, the physiological measurement comprising: a physiological parameter of the individual related to circadian phase, and a physiological measurement time comprising a time at which the physiological parameter is measured;

receiving one or more light stimulus measurements corresponding to light exposure to which the individual is exposed, the light stimulus measurements occurring between the initial time and the physiological measurement time, and wherein each light stimulus measurement comprises: a light stimulus intensity value, and light measurement time comprising a time at which the light stimulus intensity value is measured;

predicting a value of the circadian phase offset model variable corresponding to the physiological measurement time by applying the biomathematical model to at least the received estimate of the circadian phase offset corresponding to the initial time and the received one or more light stimulus measurements; and updating the predicted value of the circadian phase offset model variable corresponding to the physiological measurement time by applying the biomathematical model to at least the predicted value of the circadian offset model variable corresponding to the physiological measurement time and the received physiological measurement;

wherein for each repetition of steps the received estimate of the circadian phase of the individual corresponding to the initial time comprises the updated predicted circadian phase corresponding to the physiological measurement time from the prior repetition of steps.

13. A system according to claim 1 wherein the at least one physiological measurements comprise one or more of: core body temperature (CBT) of the individual; cortisol level of the individual; melatonin level of the individual; an activity level of the individual; a rate of cell proliferation of the individual; a parameter related to a cardiac regulatory system of the individual; a parameter related to the chemoreceptive respiratory feedback system of the individual; and a parameter related to the cognitive performance of the individual.

14. A system according to claim 1 comprising one or more light sensor devices for measuring light intensity and for estimating the light stimulus to which the individual is exposed to thereby provide the one or more light stimulus measurements received at the processor.

15. A system according to claim 1 comprising one or more light estimation devices which estimate the light stimulus to which the individual is exposed based on criteria other than light measurement to thereby provide the one or more light stimulus measurements received at the processor.

16. A system according to claim 1 wherein the at least one physiological sensor comprises a plurality of physiological sensors.

17. A method, using a processor, for predicting a circadian state of an individual, the method comprising:
providing a biomathematical model comprising:
one or more model variables comprising at least a circadian phase offset model variable representative of a phase offset of the circadian state of the individual,
at least one light stimulus model input representative of light stimulus to which the individual is exposed over time, and
at least one physiological parameter model input representative of one or more physiological parameters of the individual related to circadian phase;
wherein the biomathematical model predicts the change of the circadian phase offset model variable over time based at least in part on light exposure to which the individual is exposed over time using the at least one light stimulus model input, and updates the one more model variables based on the physiological parameter model input;

receiving an estimate of the circadian phase offset of the individual corresponding to an initial time;

receiving a physiological measurement from the physiological sensors, the physiological measurement comprising: a physiological parameter of the individual related to circadian phase, and a physiological measurement time comprising a time at which the physiological parameter is measured;

receiving one or more light stimulus measurements corresponding to light exposure to which the individual is exposed, the light stimulus measurements occurring between the initial time and the physiological measurement time, and wherein each light stimulus measurement comprises: a light stimulus intensity value, and light measurement time comprising a time at which the light stimulus intensity value is measured;

predicting a value of the circadian phase offset model variable corresponding to the physiological measurement time by applying the biomathematical model to at least the received estimate of the circadian phase offset corresponding to the initial time and the received one or more light stimulus measurements; and updating the predicted value of the circadian phase offset model variable corresponding to the physiological measurement time by applying the biomathematical model to at least the predicted value of the circadian offset model variable corresponding to the physiological measurement time and the received physiological measurement and selecting a recommended time for performing a desired action based upon the estimate of an updated PDF of the phase offset.

18. A method according to claim 17 wherein predicting a value of the circadian phase offset model comprises incorporating process noise into the model, the process noise additive, such that it may be added to a state transition equation of the model.

19. A method according to claim 17 wherein updating the predicted value of the circadian phase offset model variable comprises incorporating measurement noise into the model, the measurement noise additive, such that it may be added to a measurement equation of the model.

20. A method according to claim 17 wherein the desired action comprises one or more of: undergoing medical or chronotherapeutic treatment, application a fatigue countermeasure, modifying a sleep or work schedule, implementing occupational or environmental safety precautions, and making personnel changes.

21. A method according to claim 17 wherein the recommended time comprises one or more of: a time associated with a work or sleep schedule, a time associated with a medical diagnosis or medical treatment, a time associated with hazardous activity, and a time associated with increased risk of fatigue-related loss.

22. A computer program product embedded in a non-transitory memory medium comprising computer-readable instructions, which when executed by a suitably configured processor, cause the processor to perform a method for predicting a circadian state of an individual, the method comprising:
providing a biomathematical model comprising:
one or more model variables comprising at least a circadian phase offset model variable representative of a phase offset of the circadian state of the individual,
at least one light stimulus model input representative of light stimulus to which the individual is exposed over time, and at least one physiological parameter model input representative of one or more physiological parameters of the individual related to circadian phase;

wherein the biomathematical model predicts the change of the circadian phase offset model variable over time based at least in part on light exposure to which the individual is exposed over time using the at least one light stimulus model input, and updates the one more model variables based on the physiological parameter model input;

receiving an estimate of the circadian phase offset of the individual corresponding to an initial time;

receiving a physiological measurement from the physiological sensors, the physiological measurement comprising: a physiological parameter of the individual related to circadian phase, and a physiological measurement time comprising a time at which the physiological parameter is measured;

receiving one or more light stimulus measurements corresponding to light exposure to which the individual is exposed, the light stimulus measurements occurring between the initial time and the physiological measurement time, and wherein each light stimulus measurement comprises: a light stimulus intensity value, and light measurement time comprising a time at which the light stimulus intensity value is measured;

predicting a value of the circadian phase offset model variable corresponding to the physiological measurement time by applying the biomathematical model to at least the received estimate of the circadian phase offset corresponding to the initial time and the received one or more light stimulus measurements; and updating the predicted value of the circadian phase offset model variable corresponding to the physiological measurement time by applying the biomathematical model to at least the predicted value of the circadian offset model variable corresponding to the physiological measurement time and the received physiological measurement.

* * * * *